United States Patent
Abbate et al.

(10) Patent No.: US 9,446,225 B2
(45) Date of Patent: Sep. 20, 2016

(54) DEVICES AND METHODS FOR DILATING TISSUES

(75) Inventors: Anthony J. Abbate, Santa Clara, CA (US); Gail M. Zaler, Milpitas, CA (US); Richard E. Kaufman, Los Gatos, CA (US); David C. Gale, San Jose, CA (US); Bin Huang, Pleasanton, CA (US); Susan P. Stimson, Menlo Park, CA (US)

(73) Assignee: INTERSECT ENT, INC., Menlo Park, CA (US)

( * ) Notice: Subject to any disclaimer, the term of this patent is extended or adjusted under 35 U.S.C. 154(b) by 638 days.

(21) Appl. No.: 12/693,336

(22) Filed: Jan. 25, 2010

(65) Prior Publication Data

US 2010/0211093 A1    Aug. 19, 2010

Related U.S. Application Data

(60) Provisional application No. 61/146,987, filed on Jan. 23, 2009.

(51) Int. Cl.
*A61M 29/00* (2006.01)
*A61M 29/02* (2006.01)
(Continued)

(52) U.S. Cl.
CPC ........... *A61M 29/02* (2013.01); *A61B 17/0218* (2013.01); *A61B 17/3468* (2013.01); *A61B 17/0206* (2013.01); *A61B 17/0293* (2013.01)

(58) Field of Classification Search
CPC ........... A61M 29/00–29/02; A61M 2029/025; A61M 3/0291; A61M 25/04; A61B 17/02–17/0218; A61B 2017/0212–2017/0225

USPC .......... 606/191, 198; 604/104–109; 600/190, 600/193, 196, 201, 210, 214, 215, 219, 222, 600/224
See application file for complete search history.

(56) References Cited

U.S. PATENT DOCUMENTS 832,201 A * 10/1906 Kistler ........................... 604/108
837,085 A * 11/1906 Loar ............................. 604/108
(Continued)

FOREIGN PATENT DOCUMENTS

WO    WO-2010/085759 A1    7/2010
WO    WO-2012/083594 A1    6/2012
(Continued)

OTHER PUBLICATIONS

International Search Report mailed on Mar. 23, 2010, for PCT Patent Application No. PCT/US2010/022001 filed on Jan. 25, 2010, two pages.
(Continued)

*Primary Examiner* — Victor Nguyen
*Assistant Examiner* — Jonathan Hollm
(74) *Attorney, Agent, or Firm* — Cooley LLP

(57) ABSTRACT

Described here are devices and methods for dilating tissues. In other variations, the dilatation device comprises a slotted or expandable tube that may expand to dilate tissue. In still other variations, the dilatation device comprises two or more hinged or movable plate members that separate to dilate tissue. In yet other variations, the dilation device may comprise one or more flexible members. One or more portions of the dilatation device may be detachable from the device in the body, and dilatation device may release one or more implants into the body. In some of these variations, the dilatation device may additionally be used to expand one or more implants or other devices within the body. In some variations the dilatation device may release one or more substances that may hold dilated tissue in a dilated configuration.

10 Claims, 16 Drawing Sheets

(51) Int. Cl.
*A61B 17/34* (2006.01)
*A61B 17/02* (2006.01)

(56) References Cited

U.S. PATENT DOCUMENTS

| | | | | |
|---|---|---|---|---|
| 1,433,031 A | * | 10/1922 | Pegaitaz | 606/198 |
| 1,537,878 A | * | 5/1925 | Poirier | 604/107 |
| 1,559,737 A | * | 11/1925 | Bock | 606/198 |
| 3,704,712 A | * | 12/1972 | Giesy et al. | 606/198 |
| 3,968,800 A | * | 7/1976 | Vilasi | 606/198 |
| 5,098,392 A | | 3/1992 | Fleischhacker et al. | |
| 5,098,393 A | | 3/1992 | Amplatz et al. | |
| 5,235,966 A | * | 8/1993 | Jamner | 600/204 |
| 5,339,803 A | * | 8/1994 | Mayzels et al. | 600/201 |
| 5,522,835 A | * | 6/1996 | Tovey | 606/198 |
| 5,656,012 A | * | 8/1997 | Sienkiewicz | 600/204 |
| 5,720,763 A | * | 2/1998 | Tovey | 606/198 |
| 5,755,661 A | * | 5/1998 | Schwartzman | 600/216 |
| 5,904,649 A | * | 5/1999 | Andrese | 600/204 |
| 6,329,386 B1 | | 12/2001 | Mollison | |
| 8,721,591 B2 | | 5/2014 | Chang et al. | |
| 8,740,929 B2 | | 6/2014 | Gopferich et al. | |
| 2006/0004406 A1 | * | 1/2006 | Wehrstein et al. | 606/205 |
| 2006/0195017 A1 | | 8/2006 | Shluzas et al. | |
| 2007/0021648 A1 | | 1/2007 | Lenker et al. | |
| 2007/0250100 A1 | | 10/2007 | Schon et al. | |
| 2013/0041463 A1 | | 2/2013 | Ressemann | |
| 2013/0066358 A1 | | 3/2013 | Nalluri et al. | |
| 2013/0231693 A1 | | 9/2013 | Edgren et al. | |
| 2013/0245608 A1 | | 9/2013 | Muni et al. | |
| 2013/0253567 A1 | | 9/2013 | Edgren et al. | |
| 2013/0281982 A1 | | 10/2013 | Makower et al. | |
| 2013/0304232 A1 | | 11/2013 | Gries | |
| 2014/0018839 A1 | | 1/2014 | Renner et al. | |
| 2014/0074065 A1 | | 3/2014 | Muni et al. | |
| 2014/0107615 A1 | | 4/2014 | Doshi et al. | |

FOREIGN PATENT DOCUMENTS

| | | |
|---|---|---|
| WO | WO-2012/107229 A1 | 8/2012 |
| WO | WO-2013/158337 A1 | 10/2013 |

OTHER PUBLICATIONS

Written Opinion mailed on Mar. 23, 2010, for PCT Patent Application No. PCT/US2010/022001 filed on Jan. 25, 2010, five pages.

* cited by examiner

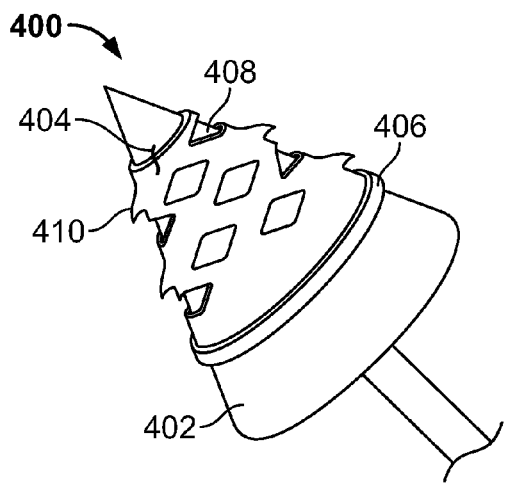
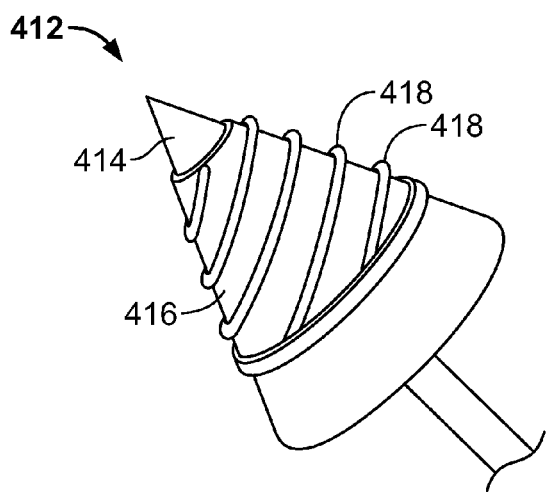
FIG. 4A
FIG. 4B
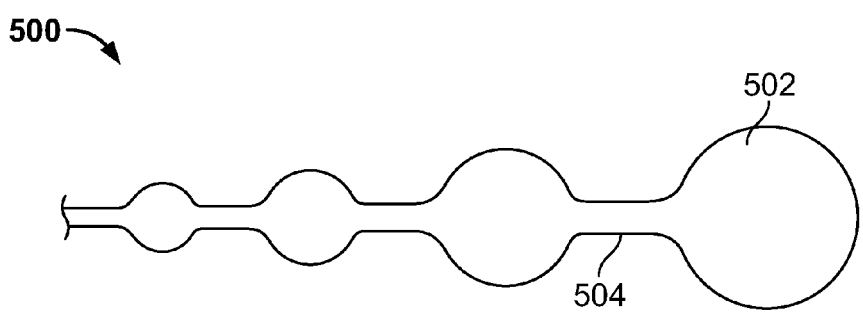
FIG. 5A
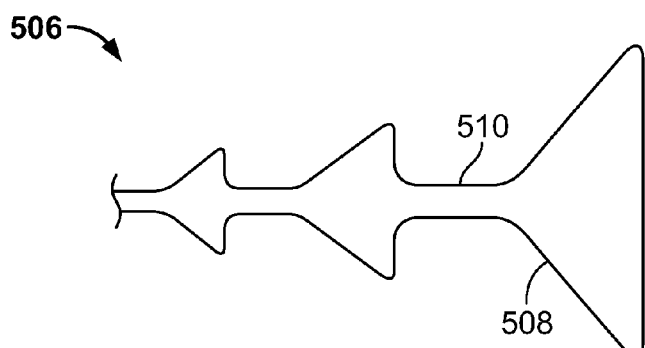
FIG. 5B

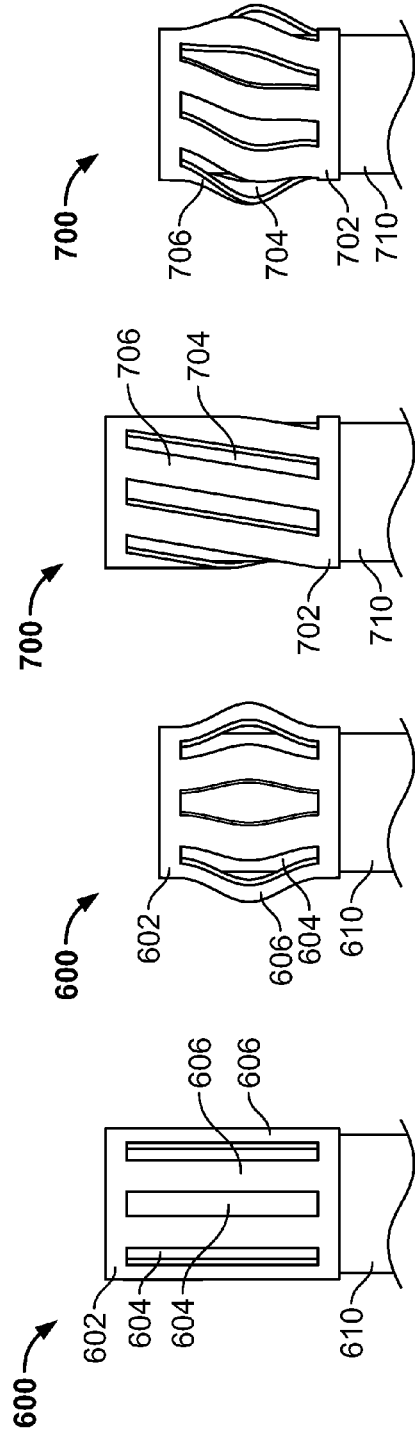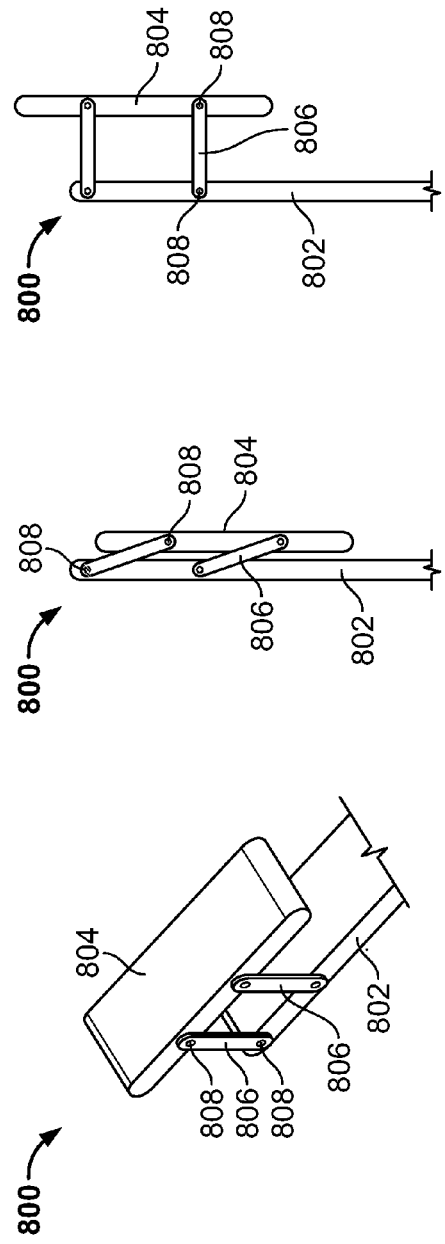

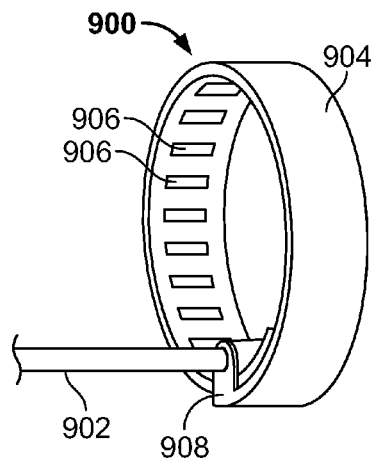
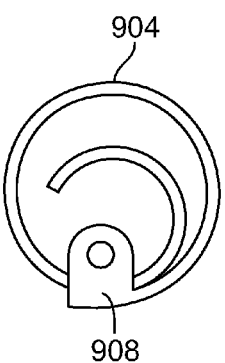
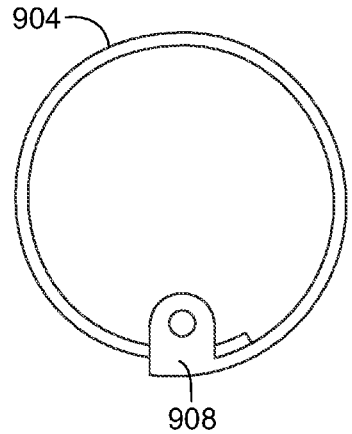
FIG. 9A  FIG. 9B  FIG. 9C
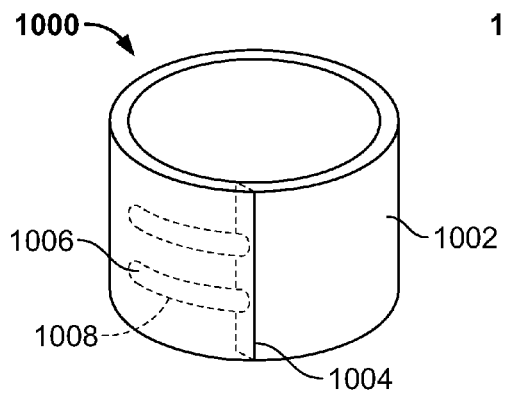
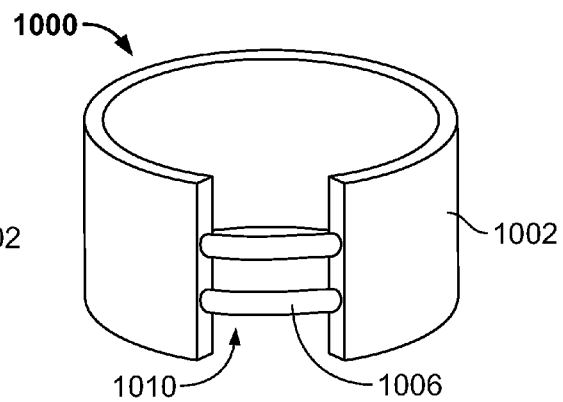
FIG. 10A  FIG. 10B
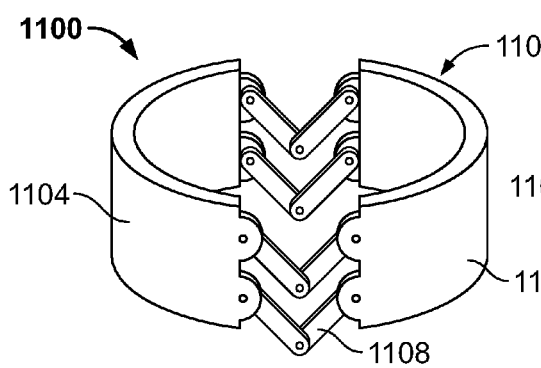
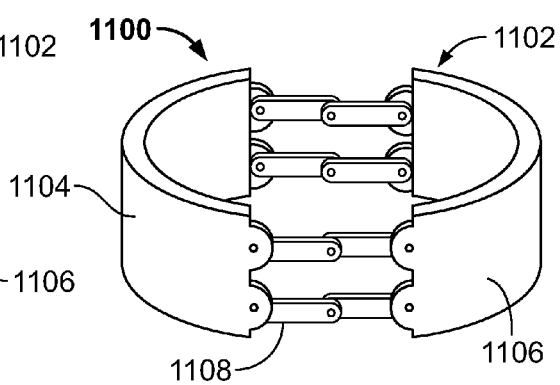
FIG. 11A  FIG. 11B

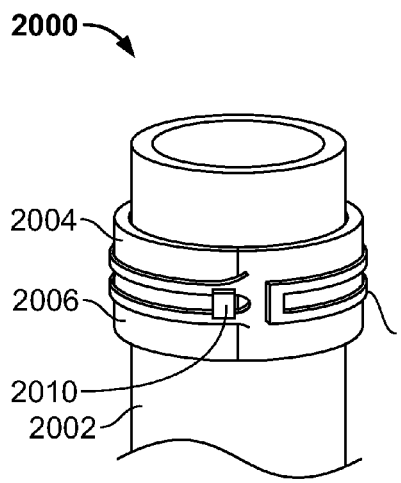
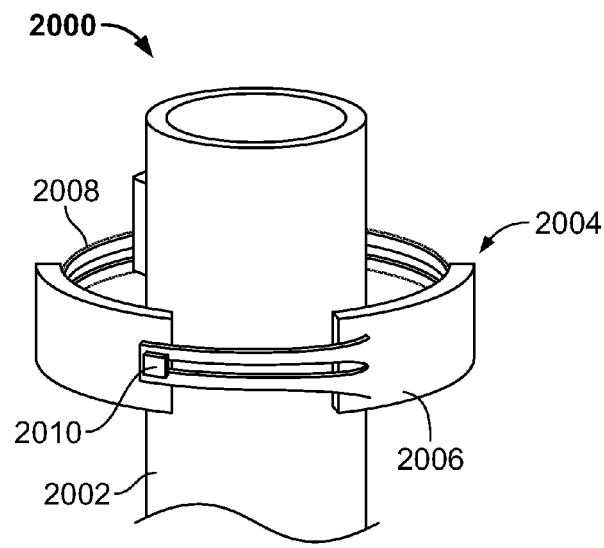
FIG. 20A  FIG. 20B
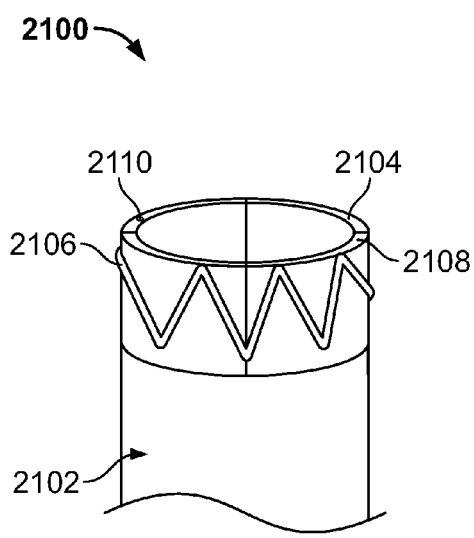
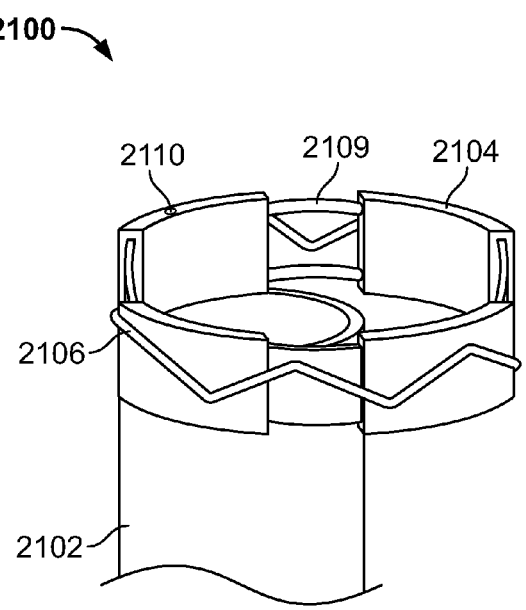
FIG. 21A  FIG. 21B

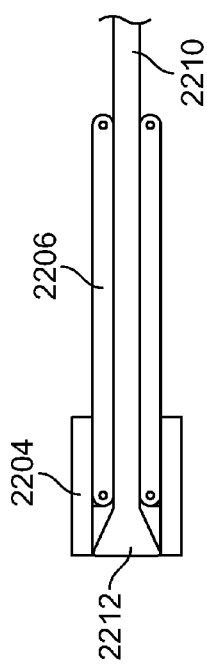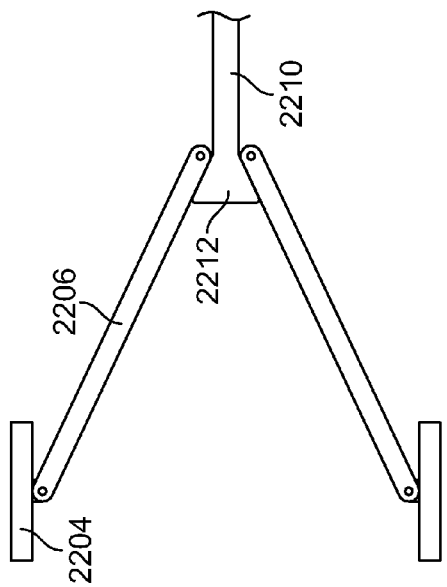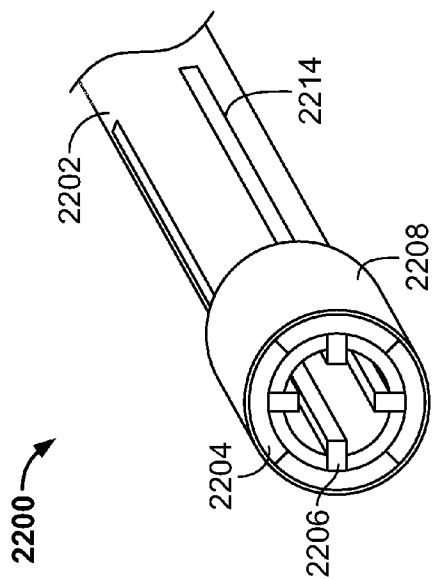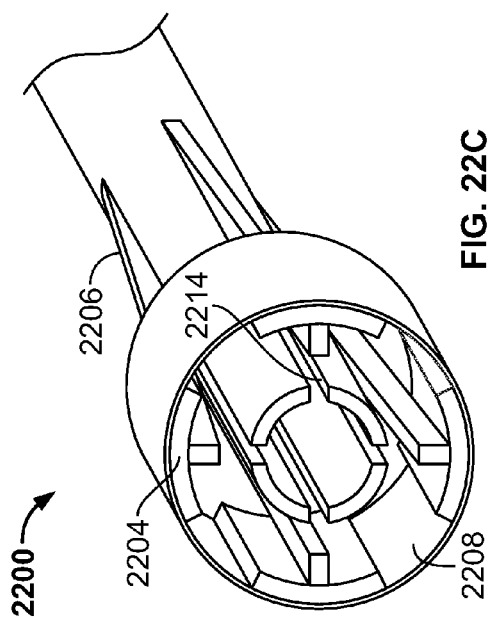

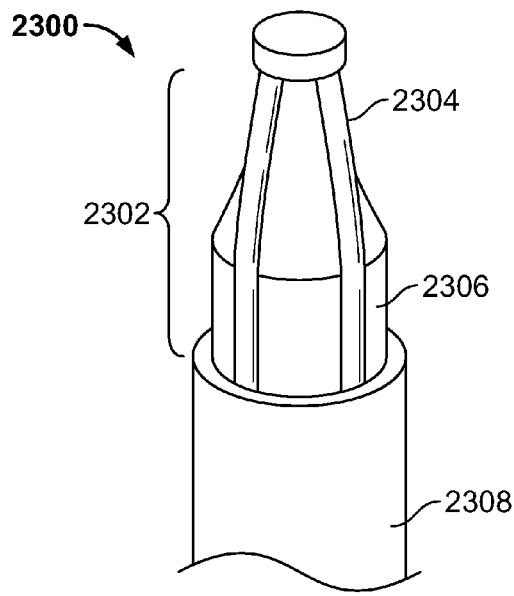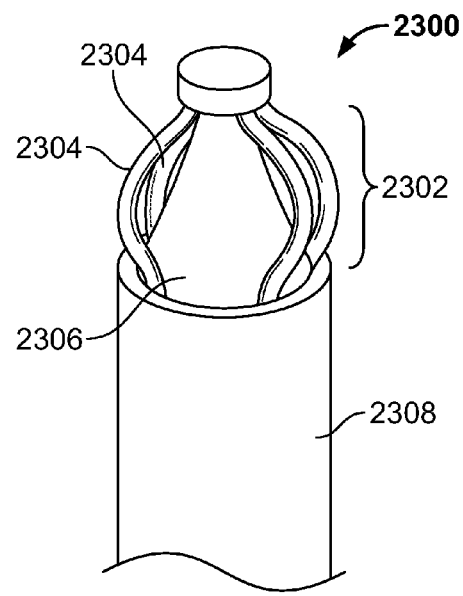
FIG. 23A   FIG. 23B
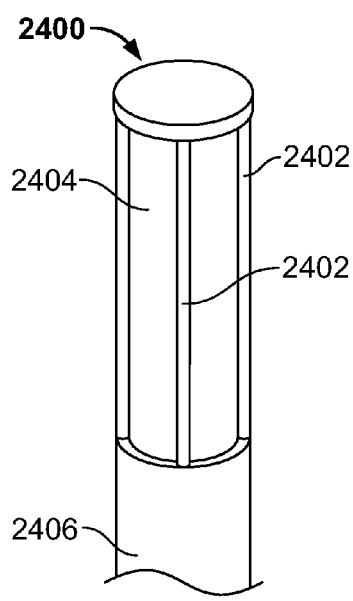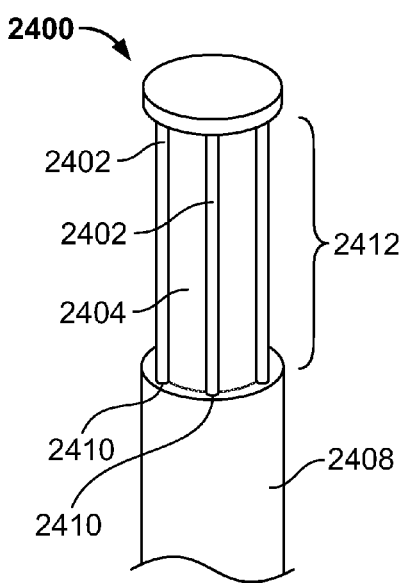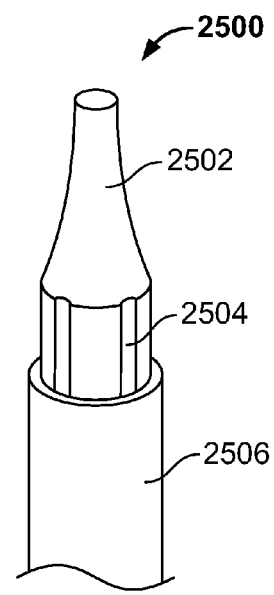
FIG. 24A   FIG. 24B   FIG. 25

DEVICES AND METHODS FOR DILATING TISSUES

RELATED APPLICATIONS

This application claims priority to U.S. Provisional Application Ser. No. 61/146,987, filed on Jan. 23, 2009, which is hereby incorporated by reference in its entirety.

FIELD

The present invention relates generally to devices and methods for dilating one or more tissues, and for expanding and/or delivering one or more implants.

BACKGROUND

When performing some interventional or surgical procedures, it may be necessary for a physician to advance one or more devices through an anatomical passageway, such as those of the ear, nose, and throat. Advancing devices through the anatomy, however, may prove difficult due to the overall size or shape of the anatomical passageway, tissue inflammation, the presence of intervening tissues or one or more other similar factors. As a result, it may be desirable to reconfigure the size or shape of the anatomical passageway or the tissues therein in order to facilitate the passage of devices therethrough. Additionally, this dilatation may also allow for the introduction or drainage of gases or fluids that would otherwise be blocked by the anatomical passageway. As such, devices that dilate one or more tissues in an anatomical passageway may be desirable.

BRIEF SUMMARY

Described here are methods and devices for dilating one or more tissues. In some of the dilatation devices described here, a tapered tube may be used to dilate one or more tissues. Generally, the tapered tube may be advanced to a target tissue, and a portion of the tapered tube may be advanced into the target tissue to dilate the tissue. In some variations, the tapered tube is collapsible. In other variations, the tapered tube comprises one or more ports or capsules. The tapered tube may additionally be used to deliver one or more implants to the body.

In other variations, one or more slotted tubes may be used to dilate tissue. Generally, the slotted tube may be advanced to a target tissue, and a portion of the slotted tube may be expanded to dilate tissue. In some variations, compressing the slotted tube may cause the slotted tube to expand. In other variations, rotation of the slotted tube may cause the slotted tube to expand. In other variations, the slotted tube may be released from the dilatation device inside of the body. Additionally, the slotted tube may expand and/or release one or more implants into the body.

In still other variations, one or more expandable tubes are used to dilate tissue. Generally, the expandable tube may be advanced to a target tissue, and a portion of the expandable tube may be expanded to dilate tissue. In some variations, the expandable tube comprises two or more separate tube segments. In other variations, the expandable tube comprises one or more hinged arms, tracks, rods, or a combination thereof. The expandable tube may or may not expand and/or release one or more implants into the body. Additionally, the expandable tube may or may not be released from the dilatation device into the body.

In some variations, one or more flexible members may be used to dilate tissue. Generally, the flexible members may be advanced in a low-profile configuration to a target tissue, and the flexible members may be expanded to dilate tissue. In some of these variations, a movable sheath may adjust the amount of the flexible members that contacts surrounding tissue. In other variations, one or more hoops may be used to dilate tissue. Generally, the hoop may be advanced to a target tissue, and a portion of the expandable hoop may be expanded to dilate tissue. In some variations, the dilatation device comprises a winder, and rotation of the winder causes the hoop to expand.

In still other variations, two or more hinged plate members may be used to dilate tissues. In some of these variations, the two or more hinged plates may be connected by at least one arm member to form a plate assembly, and a portion of the plate assembly may be expanded to dilate tissue. In some variations, one or more portions of the plate assembly may be rotatable relative to the rest of the device.

BRIEF DESCRIPTION OF THE DRAWINGS

FIGS. 4A and 4B depict illustrative variations of implants that may be delivered from the devices described here.

FIGS. 5A and 5B illustrate two variations of the dilatation devices described here.

FIGS. 6A, 6B, 7A and 7B depict illustrative variations of the devices described here comprising slotted tubes.

FIG. 8A shows a perspective view of one variation of the devices described here having hinged plate members. FIGS. 8B and 8C are side views of the device of FIG. 8A.

FIG. 9A depicts a perspective view of a variation of the devices described here comprising an expandable hoop. FIGS. 9B and 9C are side views of the device of FIG. 9A.

FIGS. 10A, 10B, 11A, 11B, 12A, 12B, 13A and 13B depict various expandable tubes that may be used with the dilatation devices described here.

FIGS. 20A, 20B, 21A and 21B depict variations of the devices described here comprising expandable tubes and catheters.

FIGS. 22A and 22C show perspective views of a suitable variation of the devices described here. FIGS. 22B and 22D are cross-sectional side views of the device of FIGS. 22A and 22C.

FIGS. 23A, 23B, 24A, 24B, and 25 depict illustrative variations of devices described here comprising one or more flexible members.

DETAILED DESCRIPTION

Figure 1A:
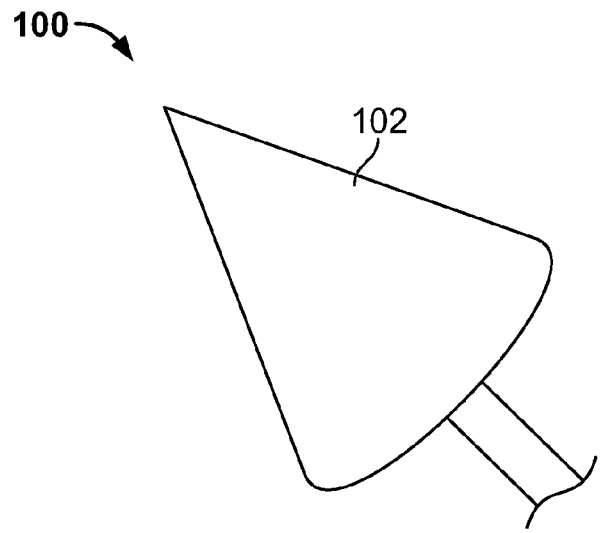
FIG. 1A is an illustrative depiction of one variation of the devices described here comprising a tapered tube.

Described here are devices and methods for dilating tissues. When reference is made to the terms "dilate," "dilation," or "dilatation" herein, it should be understood that such dilation can include, without limitation, actions such as remodeling, expanding, repositioning, changing size, shape, or configuration, combinations of the foregoing, and the like. Any dilation may or may not permanently modify tissue. Indeed, in some instances the dilatation devices may temporarily dilate one or more tissues.

The dilatation devices described here may be used to dilate any suitable tissue in any suitable anatomical passageway. In some instances, the tissue to be dilated may be located in the ear, nose, or throat. When used in the nose, dilatation devices may dilate tissue in a nasal cavity, a paranasal sinus cavity, a paranasal sinus ostium or the like. The dilatation may be used to dilate inflamed tissues, or to displace tissue structures such as nasal polyps. It should also be appreciated that although generally mentioned as being used to dilate tissue in a naturally occurring anatomical passageway, the devices described here may also be used to dilate tissue in an artificially-created passageway, opening, or cavity. The nature and dimensions of the tissue to be dilated, as well as the amount of dilation that is desirable for that tissue, may at least partially dictate one or more dimensions of the devices described here.

Dilation of tissues may provide numerous benefits in the body. In some instances, dilation of tissues may increase the size of an anatomical passageway, which may facilitate advancement of one or more other devices therethrough. For example, inflamed nasal polyps in the nasal cavities may block access to a paranasal sinus ostium. Dilation of the nasal polyps may create a space through which the paranasal sinus ostium may be accessed. In other instances, dilation of a tissue or tissues may allow mucous or other bodily fluids to drain out of the dilated tissue, or may allow one or more fluids to be introduced therethrough. In still other instances, dilation of a tissue may increase the amount of airflow that may occur through a given passageway. This increase in airflow may help to alleviate breathing difficulties or may prevent bacterial growth by increasing the amount of oxygen that reaches one or more tissues.

The devices described here may have one or more elements that may be used to dilate tissue. In some variations, a dilatation device comprises one or more tapered tubes or other structures that may be pushed into or pulled at least partially through tissue to dilate the tissue. In other variations, the dilatation device comprises a slotted or expandable tube that may expand to dilate tissue. In still other variations, the dilatation device comprises two or more hinged or movable plate members that separate to dilate tissue. One or more portions of the dilatation device may or may not be detachable from the device in the body, and dilatation device may or may not additionally release one or more implants into the body. In some of these variations, the dilatation device may additionally be used to expand one or more implants or other devices within the body, which may in turn allow for better apposition against tissue. In some variations the dilatation device may release one or more substances that may hold dilated tissue in a dilated configuration. All of these variations will be described in more detail below, and it should be realized that any number of elements and features may be combined as appropriate for a given situation.

To dilate a target tissue, one or more portions of a dilation device may first be advanced to a target tissue. To do this, for example, a distal end of the dilatation device may be introduced into the body. In some variations, the distal end of the dilatation device may be introduced into a natural opening in the body, such as an ear canal, the mouth, or a nostril. In other variations, the distal end of the dilatation device may be introduced into an artificially-created opening in the body. In some of these variations, the artificially-created opening may be preformed using one or more tools (e.g. a tissue punch) that are separate from the dilatation device. In other variations, a portion of the dilatation device may be used to create the opening.

Once the distal end of the dilatation device has gained access to the body, at least a portion of the dilatation device may then be advanced to a target location. In some variations, this advancement occurs under direct visualization. The direct visualization may be achieved by a device external to the dilatation device, such as an endoscope, or may be achieved by one or more visualization devices attached to or otherwise disposed within, on, or around a portion of the dilatation device. In some of these variations, the dilatation device may be releasably coupled to one or more endoscopes or other visualization devices. In other variations, the advancement occurs under indirect visualization, such as fluoroscopy or ultrasound. In some variations, the dilatation device may be advanced to a target site through one or more catheters, sheathes, guides, or other tubular structures. In other variations, the dilatation device may be passed along a guidewire. In still other variations, at least a portion of the dilatation device may be articulable or otherwise steerable.

During advancement, it may be desirable to provide an anesthetic or other numbing drug to help minimize pain associated with the procedure. In some variations, the dilatation device may comprise a cannula or lumen that is capable of spraying or ejecting one or more fluids or gases. The fluid or gas may or may not comprise one or more drugs. In other variations, one or more portions of the dilatation device may comprise a coating that releases one or more drugs.

Figure 1B:
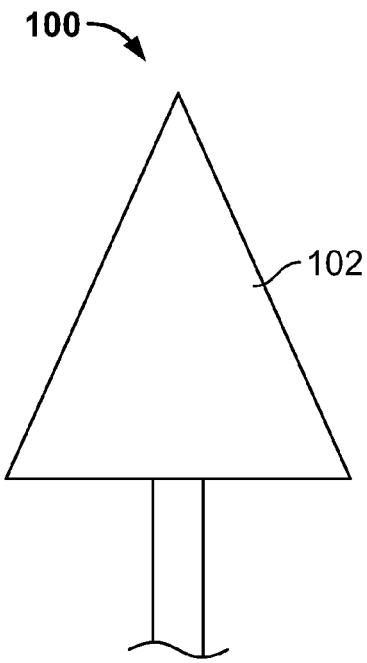
FIG. 1B is a side view of the device of FIG. 1A.

In some variations of the dilation devices described here, at least a portion of the dilatation device comprises one or more tapered tubes. Generally, the size and/or shape of the tapered tube's cross section may change along its length. For example, FIGS. 1A and 1B depict a perspective and a cross-sectional side view, respectively, of one variation of dilatation device (100) comprising a tapered tube (102). As shown in FIGS. 1A and 1B, the cross-sectional area of tapered tube (102) increases from the distal end to the proximal end of the tapered tube (102). By advancing the tapered tube (102) at least partially through a target tissue (not shown), the increasing cross-sectional area of the tube (102) passing through the tissue may dilate the tissue.

While shown in FIGS. 1A and 1B as having a circular cross-section, the tapered tube (102) may have any suitable cross-sectional shape. Indeed, the tapered tube (102) may have a cross-sectional shape that is a circle, an oval, a triangle, a square, a rectangle, a trapezoid, a rhombus, a polygon, a shape with irregular geometry, a combination thereof, or the like. Furthermore, the cross-sectional shape of the tapered tube (102) may or may not change along the length of the tapered tube. For example, in some variations the tapered tube (102) may have one or more sections that have a circular cross-section, and one or more sections that have a rectangular cross-section. In variations where the cross-sectional shape of the tapered tube (102) changes along the length of the tapered tube, this change in shape may act to reconfigure a target tissue as the tapered tube (102) is advanced into or through a passageway.

Figure 17A:
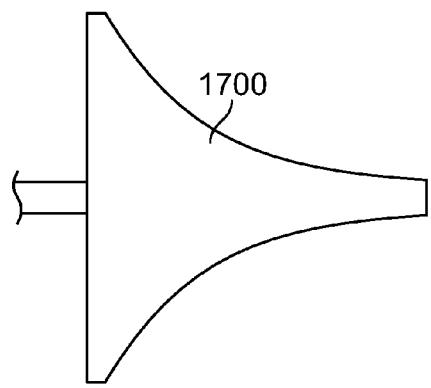
FIGS. 17A-17D, 18 and 19 depict various tapered tubes that may be suitable for use with the devices described here.
Figure 17B:
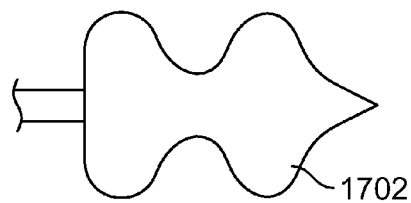
Figure 17C:
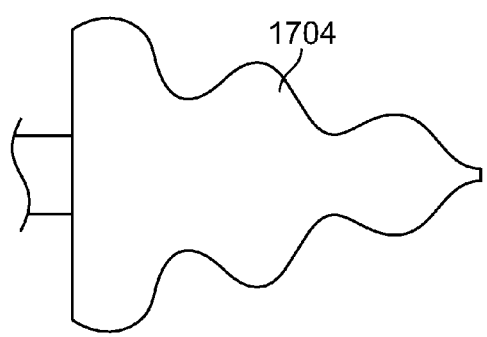
Figure 17D:
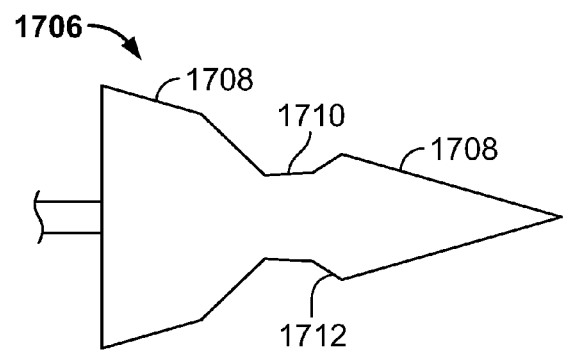

In variations where the cross-sectional area of the tapered tube (102) changes along the length of the tapered tube (102), this change may or may not follow a pattern or patterns. For example, the cross-sectional area of tapered tube (102) shown in FIGS. 1A and 1B grows at a linear, or constant, rate, from its distal to its proximal end. FIGS. 17A-17D illustrate other variations of tapered tubes that have cross-sectional areas which change according one or more patterns. FIG. 17A illustrates tapered tube (1700) which has a cross-sectional area that grows at an exponential rate from its distal to its proximal end. FIG. 17B illustrates a tapered tube (1702) that has a cross-sectional area that varies according to a sinusoidal pattern. In other variations, the cross-sectional area may change according to an increasing sinusoidal pattern, such as tapered tube (1704) shown in FIG. 17C. In still other variations, the change in cross-sectional area may not follow any particular pattern. Alternatively, in some variations the tapered tube may change according to different patterns along different portions of its length. The tapered tube may or may not have sections where the cross-sectional area does not change, where the cross-sectional area increases, where the cross-sectional area decreases, or a combination thereof. FIG. 17D shows one such variation of tapered tube (1706) with increasing-area sections (1708), constant-area sections (1710) and decreasing-area sections (1712).

The tapered tube may be made out of any suitable or desirable material or combination of materials. Examples of suitable materials include, but are not limited to polyvinyl chloride, Pebax®, polyethylene, silicone rubber, polyurethane, and any analogs, homologs, congeners, copolymers, congeners, and mixtures thereof. In some variations, the tapered tube may comprise one or more metals or metal alloys, such as, but not limited to stainless steel, magnesium, nickel-cobalt alloys, nickel-titanium alloys, copper-aluminum-nickel alloys, copper-zinc-aluminum-nickel alloys, combinations thereof, and the like. In some variations, different sections of the tapered tube (102) may be made of different materials. The tapered tube (102) may or may not be substantially rigid. Indeed, in some variations at least a portion of the tapered tube (102) may be flexible, and may be capable of bending upon application of one or more forces thereto. Tapered tubes (102) having one or more flexible portions may increase maneuverability of the tapered tube (102) when it is passed through an anatomical passageway, as it may be able to at least partially conform to bends, curves and turns in the anatomical passageway.

Figure 18:
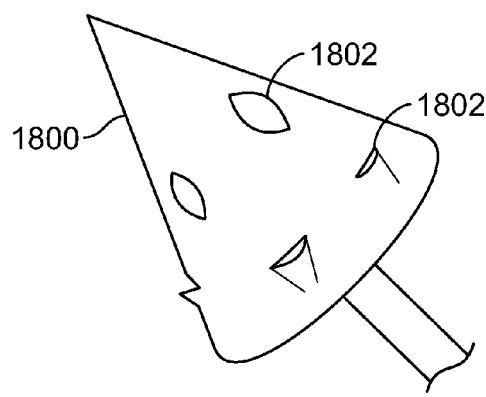

Additionally, the tapered tube here described may have any suitable additional features or combinations of features. For example, in some variations the tapered tube may have one or more textured surfaces. In some of these variations, the textured surfaces may comprise one or more ribs, ridges, bumps, studs, protrusions or indentations. In other variations, the tapered tube may comprise one or more ports. FIG. 18 shows one such variation of tapered tube (1800) comprising ports (1802). Tapered tube (1800) may comprise any number of ports (1802), and each port (1802) may have any suitable size, shape, or configuration. In some variations, ports (1802) may be used to release one or more gases or fluids from the tapered tube (1800). In other variations, ports (1802) may allow one or more fluids to drain out of the body through tapered tube (1800). In some of these variations, vacuum or suction may be applied to ports (1802).

Figure 19:
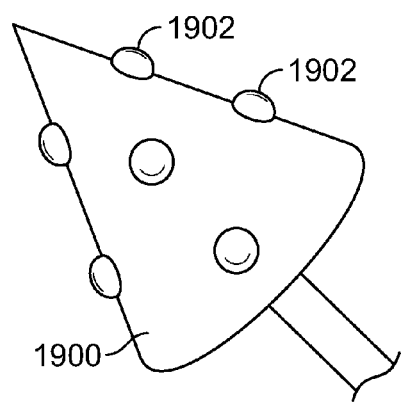

In other variations, the tapered tube may comprise one or more capsules. FIG. 19 shows one such variation of tapered tube (1900) comprising capsules (1902) disposed along the outer surface of tapered tube (1900). Capsules (1902) may house one or more gases, fluids, or gels therein. The gases, fluids, or gels may additionally include one or more drugs or agents, such as those listed below. The capsules (1902) may or may not be configured to rupture, burst, or otherwise break upon application of a certain force thereto. In some instances, as tapered tube (1900) advanced through one or more tissues, the pressure applied by the one or more tissues to the surface of tapered tube (1900) may be sufficient to rupture capsules (1902), and thereby allowing tapered tube (1900) to deliver one or more gasses, fluids, or gels to the body.

Figure 2A:
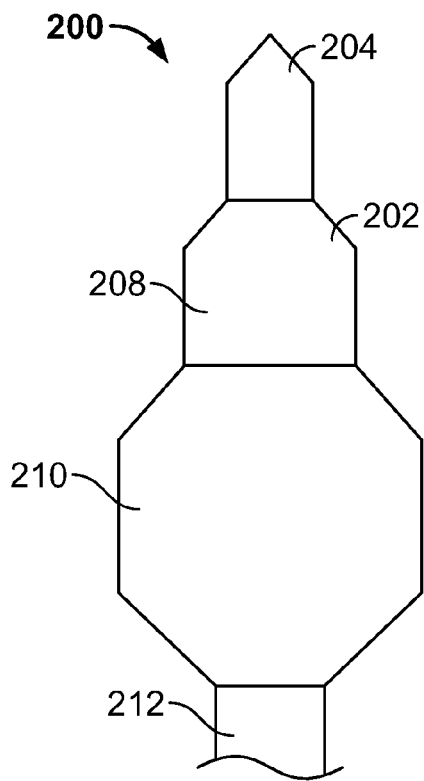
FIG. 2A is a side view of one variation of a device comprising a collapsible tapered tube.
Figure 2B:
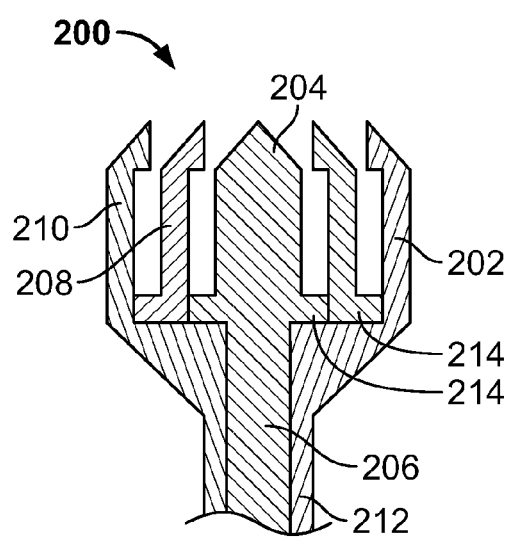
FIG. 2B is a cross-sectional side view of the device of FIG. 2A.

In some variations, the tapered tube may be at least partially collapsible to a shorter length. FIGS. 2A and 2B show a side view and a cross-sectional side view of one such variation of dilatation device (200) comprising a collapsible tapered tube (202). Shown there is tapered tube (202) comprising distal segment (204) connected to pushrod (206), middle segment (208), and proximal segment (210) attached to a catheter (212). Distal segment (204) may be capable of collapsing into middle segment (208), which in turn may be capable of collapsing into proximal segment (210). When distal (204) and middle (208) segments are collapsed into the proximal segment (210), the tapered tube (202) takes on a "collapsed" configuration, as shown in FIG. 2B.

When the tapered tube (202) of dilatation device (200) is in a collapsed configuration, it may be more easily advanced through bends, curves, or turns of an anatomical passageway, in part due to the reduced length of the tapered tube (202). After the collapsed tapered tube (202) has been advanced to a target tissue, the tapered tube (202) may be opened to its full length, as shown in FIG. 2A. To open the tapered tube (202), a user may advance pushrod (206) to advance distal segment (204) relative to the middle segment (208). Once distal segment (204) is fully advanced relative to middle segment (208), protrusions (214) of distal segment (204) may engage middle segment (208). This engagement may advance both distal (204) and middle (208) segments relative to proximal segment (210), thereby opening the tapered tube (202) to its full length.

While shown in FIGS. 2A and 2B as having three different segments (proximal, middle, and distal), a collapsible tapered tube (202) may comprise any number of discrete segments. Indeed, a collapsible tapered tube (202) may comprise two, three, four, five, six, or seven or more discrete segments. Each segment may have any suitable size, shape, or configuration. Furthermore, any suitable structure or method may be used to advance one or more tapered tube segments. In some variations, pressure applied by one or more gases or fluids may be used to open a collapsed tapered tube, while vacuum applied thereto may be used to collapse the tapered tube. In other variations, one or more balloons may be inflated to open a collapsed tapered tube, or may be deflated to collapse a tapered tube. In still other variations, one or more pushing structures such as a pushrod, a hollow tube or catheter, a wire, or the like are used to collapse or open the tapered tube. In some variations, such as that shown in FIGS. 2A and 2B, a single pushing structure is used to advance all of the movable segments relative to a catheter. In other variations, multiple pushing structures are used to advance or collapse different segments. In variations including multiple pushing structures, some of the pushing structures may be disposed within other pushing structures.

In variations that include one or more pushing structures, a user may manually advance or withdraw the one or more pushing structures, but need not. Indeed, in some variations, the pushing structures may be pneumatically controlled, mechanically controlled, robotically controlled, or a combination thereof. In these variations, a user may activate one or more pneumatic, mechanical, or robotic controls to advance or collapse certain segments, and this may thereby reduce the amount of effort a user must exert to dilate tissue. It should be noted that any of the dilatation devices described here may be configured to minimize the amount of effort, force, or exertion that a user must input in order to dilate tissue.

Figure 3A:
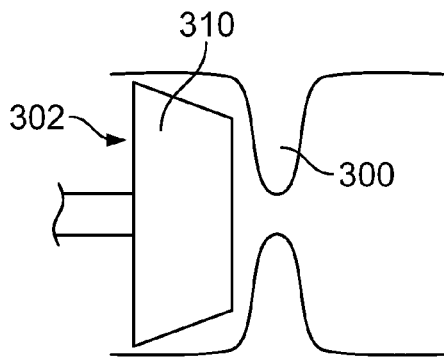
FIGS. 3A-3F depict an illustrative method of dilating a tissue using a collapsible tapered tube.
Figure 3D:
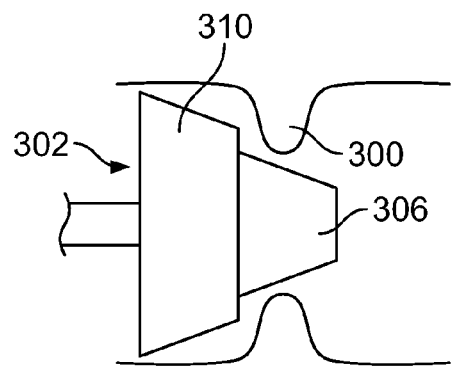
Figure 3B:
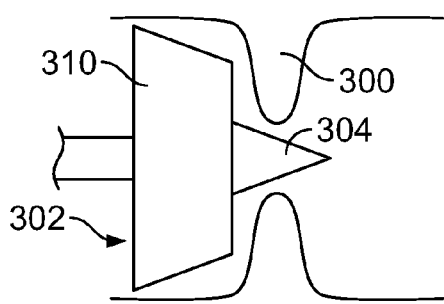
Figure 3E:
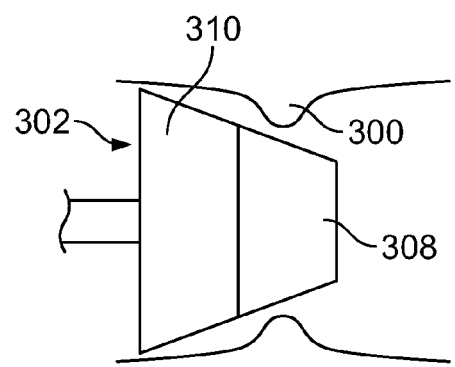
Figure 3C:
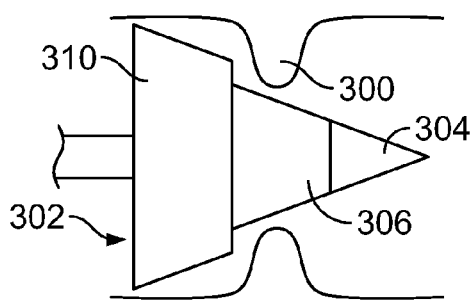
Figure 3F:
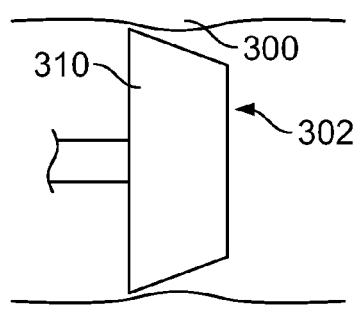

In addition to allowing for greater maneuverability, a collapsible tapered tube may be used to dilate a target tissue without having to open the tapered tube to its full length. Indeed, in variations where different segments are controlled by different pushing structures, as some segments are advanced to dilate a target tissue, other segments that have already been passed through target tissue may be collapsed. FIGS. 3A-3F illustrate one method of dilating a target tissue (300) using a collapsible tapered tube (302) comprising first (304), second (306), third (308), and fourth (310) segments. Tapered tube (302) may be advanced to the target tissue (300) in a collapsed configuration, as shown in FIG. 3A. Once in place, first segment (304) may be advance relative to the rest of tapered tube (302) to begin dilating target tissue (300), as shown in FIG. 3B. Once first segment (304) is fully advanced relative to second segment (306), second segment (306) may be advanced to further dilate the tissue. As second segment (306) is advanced, first segment (304) may move past the target tissue (300), as shown in FIG. 3C. Once past the target tissue (300), first segment (304) may be collapsed relative to second segment (306), as shown in FIG. 3D. The remaining segments may be advanced and collapsed in a similar fashion. For example, third segment (308) may be advanced into the target tissue (300), and second segment (306) may be collapsed relative to third segment (308), as shown in FIG. 3E. Finally, fourth segment (310) may be advanced through the target tissue (300), and third segment (308) may be collapsed relative to fourth segment (310) to completely collapse the tapered tube (302), as shown in FIG. 3F.

In some variations, the tapered tube may include or comprise a cover (not shown), but need not. In variations where the tapered tube is collapsible, the cover may allow the tapered tube to be collapsed or opened without interference from bodily fluids or tissues. In other variations, the cover may serve to provide a cushion between part or all of the tapered tube and surrounding tissue. The cover may be made from any suitable biocompatible material. Examples of suitable materials include, but are not limited to, silicone. In some variations, the cover may loosely envelop the tapered tube. In other variations, the cover may be affixed to one or more portions of the tapered tube. It should be noted that any of the dilatation devices described here may comprise a cover, but need not.

In some variations, the dilatation device may include one or more additional components. In some variations, the dilatation device may be advanced along a guidewire. The guidewire may or may not be integral to the dilatation device. In other variations, the dilatation device may deliver and/or expand one or more implants in the body. The implant may be any suitable implant with any suitable size, shape, or configuration. In some variations, the dilatation device may deliver one or more self-expanding devices, non-expanding devices, expandable devices, swellable device, shape-changing devices, a combination thereof, or the like. The implant may or may not be biodegradable, and may or may not be later removed via aspiration or in another suitable manner. In some variations, the dilatation device may comprise one or more lumens that may house one or more implants. In these variations, the one or more implants may be ejected from the one or more lumens using a one or more fluids, gasses, or pushing structures.

The implants may or may not be configured to release one or more drugs or other agents. The implant may comprise any suitable drug or agent, and the agent selected will largely be determined by the desired use of the implant. It should be understood that the terms "agent" and "drug" are used interchangeably herein throughout, and each can be used to describe one or more non-drug agents. The implant may comprise, for example, a diagnostic agent, or may comprise a therapeutic agent. Diagnostic agents may be used, for example, in diagnosing the presence, nature, and/or extent of a disease or medical condition in a subject. Thus for example, the diagnostic agent may be any agent suitable for use in connection with methods for imaging an internal region of a patient and/or diagnosing the presence or absence of a disease in a patient.

Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, fluorescence imaging, positron emission tomography (PET), radiofrequency (RF) and microwave laser. Diagnostic agents may also include any other agent useful in facilitating diagnosis of a disease or other condition in a patient, whether or not imaging methodology is employed.

Examples of specific diagnostic agents include radio-opaque materials such as iodine or iodine-derivatives, for example, iohexal and iopamidol. Other diagnostic agents such as, for example, radioisotopes, are detectable by tracing radioactive emissions. Examples of agents detectable by MRI are generally paramagnetic agents including, but not limited to, gadolinium chelated compounds. An example of an agent detectable by ultrasound includes, but is not limited to, perflexane. An example of a fluorescence agent includes, but is not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

The implant may also comprise any suitable therapeutic agent. Suitable classes of therapeutic agents include, for example, anti-inflammatory agents, anti-allergens, anti-cholinergic agents, antihistamines, anti-infectives, anti-platelet agents, anti-coagulants, anti-thrombic agents, anti-scarring agents, anti-proliferative agents, chemotherapeutic agents, antineoplastic agents, decongestants, healing promoting agents and vitamins (for example, retinoic acid, vitamin A, depaxapanthenol, vitamin B and their derivatives), hypersomolar agents, immunomodulators, immunosuppressive agents, and combinations and mixtures thereof.

Anti-infective agents generally include antibacterial agents, antifungal agents, antiparasitic agents, antiviral agents, and antiseptics. Anti-inflammatory agents generally include steroidal and nonsteroidal anti-inflammatory agents.

Examples of antiallergic agents that may suitable for use with the described methods and implants include, but are not limited to, pemirolast potassium (ALAMAST®, Santen, Inc.), and any prodrugs, metabolites, analogs, homologues, congeners, derivatives, salts and combinations thereof. Examples of antiproliferative agents include, but are not limited to, actinomycin D, actinomycin IV, actinomycin $I_1$, actinomycin $X_1$, actinomycin $C_1$, and dactinomycin (COSMEGEN®, Merck & Co., Inc.). Examples of antiplatelet, anticoagulant, antifibrin, and antithrombin agents include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibodies, recombinant hirudin, and thrombin inhibitors (ANGIOMAX®, Biogen, Inc.), and any prodrugs, metabolites, analogs, homologues, congeners, derivatives, salts and combinations thereof.

Examples of cytostatic or antiproliferative agents that may be suitable for uses with the described methods and implants include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of antibacterial agents that may be suitable for use with the described methods and implants include, but are not limited to, aminoglycosides, amphenicols, ansamycins, β-lactams such as penicillins, lincosamides, macrolides, nitrofurans, quinolones, sulfonamides, sulfones, tetracyclines, vancomycin, and any of their derivatives, or combinations thereof. Examples of penicillins that may be suitable for use with the described methods and implants include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

Examples of antifungal agents suitable for use with the described methods and implants include, but are not limited to, allylamines, imidazoles, polyenes, thiocarbamates, triazoles, and any of their derivatives. Antiparasitic agents that may be employed include, but are not limited to, atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and implants include, but are not limited to, acyclovir, famciclovir, valacyclovir, edoxudine, ganciclovir, foscarnet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-hoxy)propyl) guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N-,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-1]-methane), NIH351, and combinations thereof.

Examples of antiseptic agents suitable for use with the described methods and implants include, but are not limited to, alcohol, chlorhexidrine, iodine, triclosan, hexachlorophene, and silver-based agents, for example, silver chloride, silver oxide, and silver nanoparticles.

Anti-inflammatory agents may include steroidal and nonsteroidal anti-inflammatory agents. Examples of suitable steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Examples of suitable nonsteroidal anti-inflammatory agents include, but are not limited to, COX inhibitors. These COX inhibitors may include COX-1 or COX nonspecific inhibitors such as, for example, salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of chemotherapeutic/antineoplastic agents that may be used in the implants described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites or other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, azathioprine, docetaxel analogs/congeners, derivatives of such compounds, and combinations thereof.

Examples of decongestants that may be used in the implants and methods described here include, but are not limited to, epinephrine, pseudoephedrine, oxymetazoline, phenylephrine, tetrahydrozolidine, and xylometazoline. Examples of mucolytics that may be used in the implants and methods described here include, but are not limited to, acetylcysteine, dornase alpha, and guaifenesin. Anti-histamines such as azelastine, diphenhydramine, and loratidine may also be used in the methods and implants described here.

Suitable hyperosmolar agents that may be used in the implants described here include, but are not limited to, furosemide, sodium chloride gel, and other salt preparations that draw water from tissue or substances that directly or indirectly change the osmolarity of the mucous layer.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells including, but not limited to prokaryotes and eukaryotes such as, for example, epithelial cells and genetically engineered epithelial cells; dexamethasone; and, any prodrugs, metabolites, analogs, homologues, congeners, derivatives, salts and combinations thereof.

Examples of free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5, 5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate, and any analogs, homologues, congeners, derivatives, salts and combinations thereof.

Figure 15A:
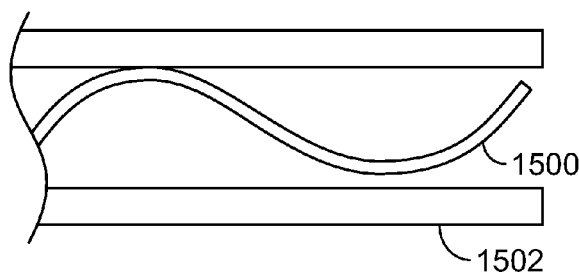
FIGS. 15A and 15B depict an implant that may be useful with the dilatation devices described here.
Figure 15B:
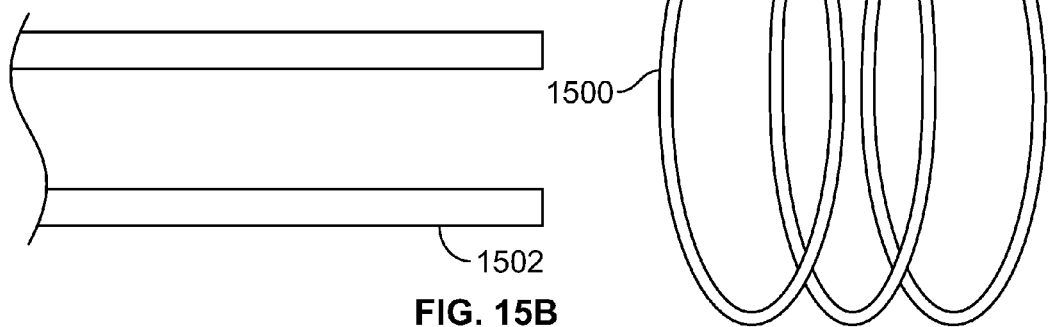

In some variations, the implant may itself be capable of dilating one or more tissues. For example, in some instances, the dilatation device may deliver a spring or coil in the body. The coil may first be passed to the target site in a low-profile configuration. In some of these variations, such as that shown in FIGS. 15A and 15B, a coil (1500) may be delivered in a low-profile configuration using a catheter (1502). Coil (1500) may be stretched or elongated, which may reduce the diameter of coil (1500), and may allow the coil (1500) to be placed in a catheter (1502), as shown in FIG. 15A. The catheter (1502) may be advanced to a target site. Once in place, the coil (1500) may be released from catheter (1502), as shown in FIG. 15B. In some variations, the coil may have a tendency to return to its original shape, which may return the coil (1500) to a shape with a diameter wider than that of catheter (1502). This return to a larger diameter may dilate surrounding tissue.

In variations where the dilatation device comprises a tapered tube, one or more implants may be disposed around or otherwise attached to a portion of the outer surface of the tapered tube. FIGS. 4A and 4B illustrate two such variations of dilatation implants having tapered tubes that may deliver one or more implants. Shown in FIG. 4A is dilatation device (400) comprising tapered tube (402) and wire (404). Also shown there is implant (406), comprising channels (408) and anchors (410). As shown in FIG. 4A, implant (406) may be sized to fit around a portion of tapered tube (402). When tapered tube (402) is advanced to dilate a target tissue, the implant (406) may be advanced therewith. Before, during, or after dilation of the target tissue, the implant (406) may be released from the tapered tube (402), as will be described in more detail below. Once released, the implant (406) may hold dilated tissue in a dilated configuration, thereby preventing the dilated tissue from returning to its original configuration.

Implant (406) may be releasably attached to tapered tube (402). In these variations, implant (406) may be attached in any suitable manner. In some variations, such as that shown in FIG. 4A, a wire (404) or other structure may hold implant (406) against tapered tube (402). Wire (404) may be flexible, bendable, severable, or otherwise deformable to allow implant (406) to be released from tapered tube (402). In variations in which the tapered tube comprises ports, suction or vacuum may applied to the implant to hold it in place. In other variations, one or more adhesives or films may attach the implant (406) to the tapered tube.

Similarly, the implant (406) may be released from tapered tube (402) in any suitable manner. In some variations, one or more pushing structures disposed in, on, or around the tapered tube may be used to release implant (406). In variations where the tapered tube comprises one or more ports, passing one or more gases or fluids through one or more ports may apply pressure to the implant, which may cause the implant (406) to disengage from the tapered tube. In variations where the implant comprises one or more anchors, barbs, tacks, prongs, or threading, as will be described in more detail below, engagement between the implant and surrounding tissue may cause the implant to disengage from the tapered tube when the tapered tube is withdrawn.

While shown in FIG. 4A as comprising channels (408) through the surface of implant (406), implant (406) need not. In variations that do include channels (408), implant (406) may comprise any number of channels (408) (e.g., one, two, three, four, five, or six or more), and each channel (408) may have any suitable size or shape. In some variations, each channel (408) may have the same size and shape. In other variations, different channels (408) may have different sizes and/or shapes. Channels (408) may allow one or more fluids or gasses to pass through the body of the implant (406). This may facilitate drainage of mucous or other bodily fluids through implant (406), or may allow for increased air contact with tissue that is held by implant (406).

The implant (406) may comprise one or more features or elements that act to hold the implant (406) in place once implanted. For example, the implant (406) may comprise one or more prongs, barbs, tacks, or other anchors (410), as shown in FIG. 4A. The implant may comprise any number of anchors (410) (e.g. one, two, three, four, or five or more), and each anchor may have any suitable size, shape, or configuration. In some variations, the anchors may be configured to help minimize tissue damage while the implant (406) is advanced through the body. For example, anchors (410) may be angled away from the distal end of the implant (406), or may have one-way flexibility that allows the anchors (410) to be pressed against the body of the implant (406). In some instances, the anchors (410) may help release the implant (406) from the tapered tube (402). When the tapered tube (402) is withdrawn from the body, the anchors (410) may be configured to engage surrounding tissue. As the tapered tube (402) continues to be withdrawn, the implant (406) may be held in place by this engagement and thus may be separated from the tapered tube (402).

FIG. 4B shows another variation of dilatation device (412) comprising tapered tube (414). Also shown there is implant (416) disposed around tapered tube (414) and comprising threading (418). Threading (418) may displace tissue when tapered tube (414) is at least partially advanced into tissue, and thus may allow implant (416) to be "screwed" into a target tissue by rotating implant (416) while that target tissue is being dilated. Once screwed into place, the tissue surrounding the threading (418) may engage implant (416), and may hold implant (416) in place relative to the tissue. Tapered tube (414) may then be withdrawn, and the tissue surrounding implant (416) may hold implant (416) in place, thereby releasing it from tapered tube (414).

In other variations of the dilatation devices described here, one or more structures may be pushed or pulled through a target tissue to dilate the tissue. As the structure is pushed or pulled through the target tissue, the tissue may change shape or otherwise reconfigure to allow passage of the structure therethrough. The structure may be any suitable structure with any suitable size or dimensions. For example, in some variations the structure may be one or more tapered tubes, as described above. In some variations, the structure may have a spherical shape, an ellipsoid shape, a conical or frustoconical shape, a box shape, a pyramidal shape, a combination thereof, or the like. When pushed through a target tissue, the structure may be advanced by any suitable pushing structure (e.g. a pushrod or rigid wire). Conversely, when pulled through a target tissue, the structure may be pulled using a pushrod or other semi-rigid structure, or may be pulled using a flexible material such as a suture, a wire, or the like.

The structure may or may not have a fixed size and shape. In some variations, the structure may partially deform in response to one or more forces applied thereto. In other variations, at least a portion of the structure may inflatable. For example, in some variations the structure may comprise a balloon. In these variations, the structure may be moved in a deflated low-profile configuration past the target tissue, may be inflated, and then may be pulled through the target tissue to dilate the target tissue.

In some variations, it may be desirable to pass structures of differing sizes through a target tissue. FIGS. 5A and 5B illustrate two such variations of dilatation devices comprising structures of multiple sizes. Shown in FIG. 5A is dilatation device (500) comprising spheres (502) of different sizes disposed along wire (504). While shown in FIG. 5A as comprising spheres (502), dilatation device (500) may comprise structures of any shape, as described above. For example, FIG. 5B shows another variation of dilatation device (506) comprising cone-shaped structures (508) of different sizes disposed along wire (510). Additionally, each structure may or may not have a different shape, and may or may not be inflatable. By passing structures of increasing size through a target tissue, an operator may dilate the target tissue incrementally. The increasing size of the structures may increasingly dilate the tissue, while the space between each structure may allow the tissue to relax or otherwise readjust between sequential dilations.

In other variations of the dilatation devices described here, a dilatation device may comprise one or more slotted tubes. FIGS. 6A and 6B illustrate one variation of dilatation device (600) comprising slotted tube (602) having slots (604) and prongs (606) and catheter (610). Generally, one end of the slotted tube (602) may be fixed relative to catheter (610), while the other end may be movable relative to the fixed end. For example, the moveable end of the slotted tube (602) may be attached to one or more inner catheters (not shown) or actuators that may pull or push on the movable end. When the movable end is moved relative to the fixed end, one or more prongs (606) may bend, flex, or deform away from dilatation device (600), as shown in FIG. 6B. This expansion of the slotted tube may push tissue away from catheter (610). In some variations, the slotted tube (602) may be detached from catheter (610) inside of the body. In some variations, the slotted tube (602) may comprise one or more barbs or anchors to hold the slotted tube (602) in place within the body. In other variations, the slotted tube (602) may be biodegradable. Additionally, the slotted tube (602) may be configured to release one or more drugs, or may comprise one or more coatings that are configured to release one or more drugs, such as those listed above. It should also be noted that although described here as a slotted tube, dilatation device may comprise any structure containing prongs or arm-like structures, and may be expanded to dilate tissue as described here.

The shape of the expanded slotted tube (602) may be dependent on the size, shape, and orientation of the slots (604) and prongs (606), as well as the manner in which the movable end of the slotted tube (602) is moved in relation to the fixed end. As such, slots (604) and prongs (606) may have any suitable size shape or orientation. Indeed, in some variations, slots (604) may be narrow enough to allow adjacent prongs (606) to maintain physical contact. Additionally, while the fixed and free ends of slotted tube (602) may be moved toward or away from each other, they may alternatively be rotated in order to expand the slotted tube (602). Indeed, FIGS. 7A and 7B illustrate one such variation of dilatation device (700) comprising a slotted tube (702) having angled slots (704) and prongs (706), and catheter (710). In this variation, rotation of a movable end of the slotted tube (702) relative to its fixed end may cause the angled prongs (706) to expand away from catheter (710), as depicted in FIG. 7B.

In other variations, the dilatation devices described here may comprise one or more flexible members that may bend or flex to dilate tissue. FIGS. 23A and 23B illustrate the distal end of one such variation of dilatation device (2300) having an adjustable dilating portion (2302). Shown there are flexible members (2304), inner member (2306), and adjustable outer sheath (2308). The distal ends of flexible members (2304) may be attached to the inner member (2306) at or near its distal end. This attachment may occur in any suitable manner, such as, for example, mechanical attachment (e.g., welding, soldering, press fitting, swaging, etc.), chemical attachment (e.g., adhesive bonding), or the like. Additionally, the flexible members (2304) may also be at least partially covered by the outer sheath (2308), leaving a portion of the flexible members (2304) uncovered. The dilating portion (2302) of device (2300) may comprise the uncovered portions of the flexible members (2304). Flexible members (2304) may be any structure capable of bending or flexing when placed under a compressive force, and capable of returning to an unbent or unflexed configuration when the compressive force is removed, such as, for example, a wire or cable. The flexible members (2304) may be made from any suitable material or materials, such as, for example, stainless steel, cobalt chrome, metal alloys (e.g., nickel-cobalt alloys, nickel-titanium alloys, copper-aluminum-nickel alloys, copper-zinc-aluminum-nickel alloys, etc.), nylon-reinforced polymer extrusions, Kevlar-reinforced polymer extrusions, braided materials, combinations thereof and the like.

To dilate tissue, the distal end of dilatation device (2300) may be advanced in a low-profile configuration to a target location, as shown in FIG. 23A. When in a low-profile configuration, the flexible members (2304) may lay approximately parallel to inner member (2306). Once in place, inner member (2306) may be pulled proximally relative to a handle portion (not shown), which may in turn apply a compressive force to flexible members (2304). This compression may cause device (2300) to change to an expanded configuration, in which the uncovered portions of flexible members (2304) bend or flex away from the device (2300), as shown in FIG. 23B. The outer sheath (2308), however, may prevent the covered portions of the flexible members (2304) from bending or flexing away from device (2300). As such, only the dilating portion (2302) (i.e., uncovered portions of flexible members (2304)) may be expanded when device (2300) is in an expanded configuration.

As mentioned briefly above, dilating portion (2302) may be adjustable. Specifically, the amount of expansion, as well as the size of the dilating portion (2302) may be adjusted. For example, the amount of expansion of the dilating portion (2310) may be dependent on the range of motion of the inner member (2306). Specifically, the further the inner member (2306) is withdrawn relative to device (2300), the more the flexible members (2304) may bend away from device (2300).

The size of dilating portion (2310) may be altered by adjusting the placement of outer sheath (2308). Specifically, outer sheath (2308) may be advanced relative to flexible members (2304) to cover a larger portion of the flexible members (2304). Covering a larger portion of the flexible members (2304) reduces the amount of the flexible members (2304) that are uncovered, and thus may reduce the effective length of dilating portion (2302). Conversely, outer sheath (2308) may be withdrawn to expose a larger portion of the flexible members (2304), and thus may increase the length of the dilating portion (2302). By allowing a user to adjust both the length of the dilating portion (2310) as well as the amount of expansion of the expandable region (2310), dilatation device (2300) may be adjusted to fit the size and expansions constraints of a target tissue region.

Although not shown in FIGS. 23A and 23B, the proximal ends of flexible members (2304) may be attached to any suitable portion of the dilatation device (2304). For example, in some variations the proximal ends of the flexible members (2304) may be attached directly to a handle portion (not shown). In other variations, the proximal ends of the flexible members (2304) may be attached to another component of the device. FIGS. 24A and 24B show one such variation of dilatation device (2400). Shown in FIG. 24A are flexible members (2402), inner member (2404), and inner sheath (2406). In this variation, the distal ends of flexible members (2402) may be attached at or near the distal end of inner member (2404) while the proximal ends of flexible members (2402) may be attached at or near the distal end of inner sheath (2406). The inner sheath (2406) may in turn be connected to a handle portion (not shown), or some other portion of the device. As shown in FIG. 24B, the flexible members (2402) may at least partially be covered by an adjustable outer sheath (2408) to define a dilating portion (2412) as descried in more detail above. Device (2400) may be use to dilate tissue as described in more detail above.

In some instances, the covered portions of the flexible members may have a tendency to wrap or twist around the inner member when the members are placed under a compressive force. As such, it may be desirable to restrain the covered portions of flexible members such that they cannot wrap or twist around the inner member. In some variations, one or more portions of the device may comprise one or more grooves or channels. At least a segment of the covered flexible members may be disposed in these grooves or channels such that they are held in place by the grooves or channels. By housing and restraining the covered portions of a flexible member, the grooves or channels may help to prevent any wrapping or twisting in that portion of the member. In some variations, such as dilatation device (2400) described with respect to FIG. 24B, at least a portion of outer sheath (2408) may comprise one or more of these grooves or channels (2410) for housing flexible members (2402). Alternatively, FIG. 25 shows another variation of dilatation device (2500) having inner member (2502) and outer sheath (2506), and in which the inner member (2502) comprises one or more grooves or channels (2504). In still other variations, both the inner member and the outer sheath may comprise one more grooves or channels.

In some variations of the dilatation devices described above having flexible members, the devices may further comprise one or more covers surrounding at least a portion of the device. The cover may be any suitable cover, such as those described in more detail above. In variations that do include a cover, the cover may serve one or more functions. In some instances, the cover may span two or more of the flexible members to support or dilate tissues that are not in direct contact with the flexible members, which may prevent tissue prolapse. In other instances, the cover may help to prevent tissue from getting caught between the inner member and one or more of the flexible members, or may protect tissue from one or more edges or other surfaces of the device. In still other instance, the cover may be used to release one or more drugs to the surrounding tissue.

Some variations of the devices described here may comprise an expandable plate assembly suitable for dilating tissue. Generally, a plate assembly may comprise two or more plate members that are attached in a hinged manner. The hinged attachment between the plate members allows the plate assembly to move between a low-profile configuration an expanded configuration. For example, FIGS. 8A-8C illustrate one such variation of a plate assembly (800) comprising a first plate member (802) and second plate member (804) connected in a hinged manner. As shown in a perspective view in FIG. 8A, first (802) and second plate member may be hingedly connected via arms (806), as shown in a perspective view in FIG. 8A. Arms (806) may be capable of rotating relative to first (802) and second (804) plate members at hinge points (808). As arms (806) rotate relative to first (802) and second (804) plate members, plate assembly (800) may move between a low-profile configuration, as shown in FIG. 8B, and an expanded configuration, as shown in FIG. 8C.

To dilate a tissue using plate assembly (800), first (802) and second (804) plate members may be placed in a low-profile configuration, as shown in FIG. 8B. This low-profile configuration may facilitate advancement of the plate assembly (800) through the anatomy, as the plates may lay flat or nearly flat against each other. Once plate assembly (800) has been advanced to a target site, first (802) and second (804) plate members may be moved to an expanded configuration to dilate surrounding tissue. To expand plate assembly (800), one or more structures (not shown) may be used to push or pull one plate member relative to the other, which may cause the arms (806) to rotate. This rotation, in turn, may cause the second plate member (804) to move away from the first plate member (802), thereby increasing the space between the plate members, as shown in FIG. 8C. In some variations, the dilatation device (800) may be expanded by inflating a balloon (not shown) between first (802) and second (804) plate members.

As shown in FIGS. 8A-8C, the entire length of second plate member (804) moves away from the first plate member (802) as the plate assembly (800) changes between low-profile and expanded configurations. In some instances, however, it may be desirable to have at least a portion of the plate members remain connected in a low-profile configuration, even when the overall plate assembly is in an expanded configuration. For example, it may be desirable to dilate a certain area of tissue without dilating nearby tissue areas. As such, in some variations a plate assembly may be configured such that a portion of two or more plate members are connected in a constrained fashion, wherein the spacing between the plate members remains fixed. In some of these variations, plate members may still be slidable relative to one another. In some variations, a plate assembly may be divided into one or more constrained regions (i.e., wherein the spacing between plate members remains fixed) and one or more expandable regions (i.e., wherein the spacing between plate members may varied to dilate surrounding tissue).

Figure 26A:
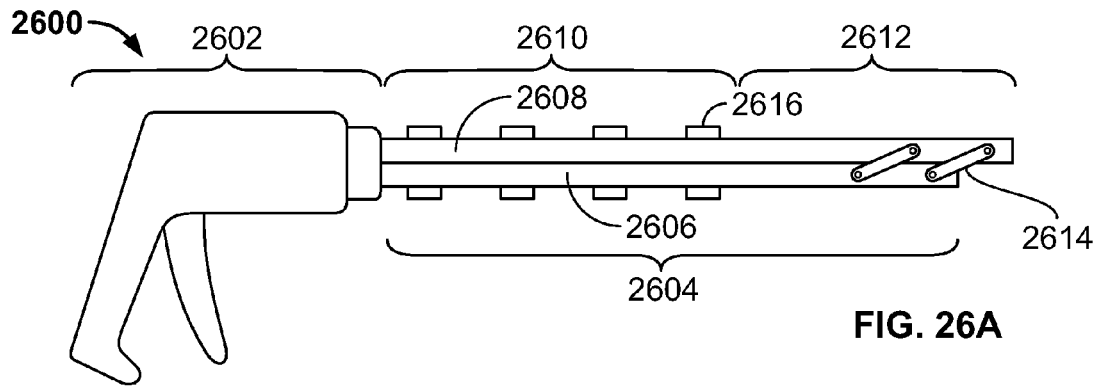
FIGS. 26A, 26B, 27A, 27B, and 28A-28D depict several illustrative variations of devices described here comprising plate assemblies.
Figure 26B:
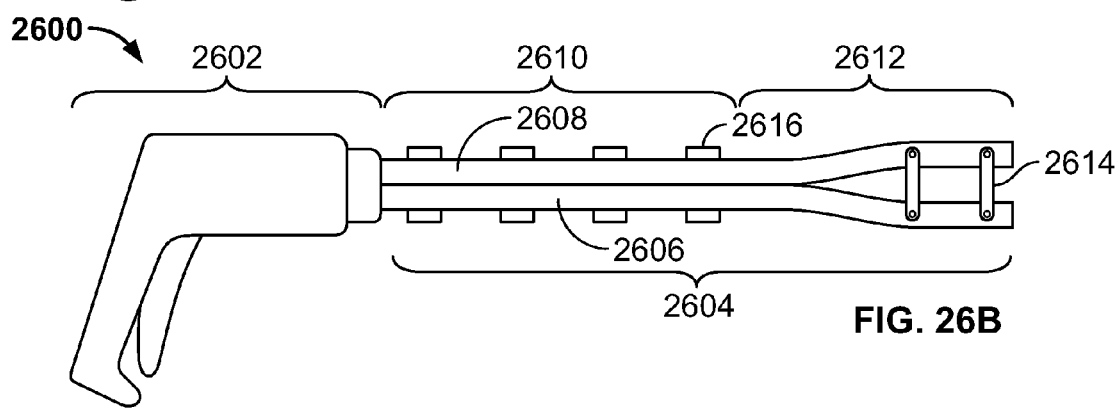

FIGS. 26A and 26B illustrate one such variation of dilatation device (2600). Shown there is handle portion (2602) with plate assembly (2604) attached thereto. Plate assembly (2604) may comprise first plate member (2606) and second plate member (2608), and may be divided into constrained region (2610) and expandable region (2612). First (2606) and second (2608) plate member may be capable of moving relative to one another to change plate assembly (2604) from a low-profile configuration, as shown in FIG. 26A, to an expanded configuration, as shown in FIG. 26B. In some variations, first plate member (2606) may be fixedly attached to handle portion (2602) while second plate member (2608) may be retracted at least partially into handle portion (2602) upon actuation of the device (2600). This retraction may cause second plate member (2608) to slide proximally relative to first plate member (2606) and may change plate assembly (2604) between low-profile and expanded configurations. After dilation, the second plate member (2608) may be advanced relative to first plate member (2606) to return plate assembly (2604) to its low-profile configuration. In other variations, the second plate member (2608) may be fixedly attached to the handle portion (2602), and the first plate member (2606) may be advanced from handle portion (2602) to change the device between low-profile and expanded configurations. The first plate member may then be withdrawn to return the device to a low-profile configuration.

To dilate tissue using device (2600), the distal end of device (2600) may advanced to a target location. The device (2600) is then actuated to change plate assembly (2604) between a low-profile and an expanded configuration. When plate assembly (2604) is changed between low-profile and expanded configurations, the expandable region (2612) may "expand" (i.e., the separation between adjacent plates may increase) while the constrained region (2610) may remain in a low-profile state. In the expandable region (2612), the first plate (2606) and second plate (2608) may be connected in a hanged manner via arms (2614) in the expandable region (2612). As second plate (2608) slides relative to first plate (2606), the arms (2614) may rotate to increase the spacing between first (2608) and second plates (2608) in the expandable region (2612), as described in more detail above with respect to FIGS. 8A-8C. As the expandable region (2612) expands, the plates may push against surrounding tissue, and may thereby dilate the surrounding tissue. Because the constrained region (2610) remains in a low-profile state, it may not dilate surrounding tissue. Following dilation, the device may be returned to a low-profile configuration and may be repositioned or removed from the body.

As illustrated in FIGS. 26A and 26B, in the constrained region (2610), a plurality of rivets (2616) connects first (2606) and second (2608) plate members. These rivets (2616) may allow for first plate member (2606) and second plate member (2608) to slide relative to each other, but may also hold them together such that the first (2606) and second (2608) cannot expand away from each other. This allows the constrained regions (2610) to remain in a low-profile state while other regions of the plate assembly (2604) are expanded. Although shown in FIGS. 26A and 26B as being joined with rivets (2616), the first (2606) and second (2608) plate members may be held in a constrained fashion in any suitable manner, such as those described in more detail below.

Figure 27A:
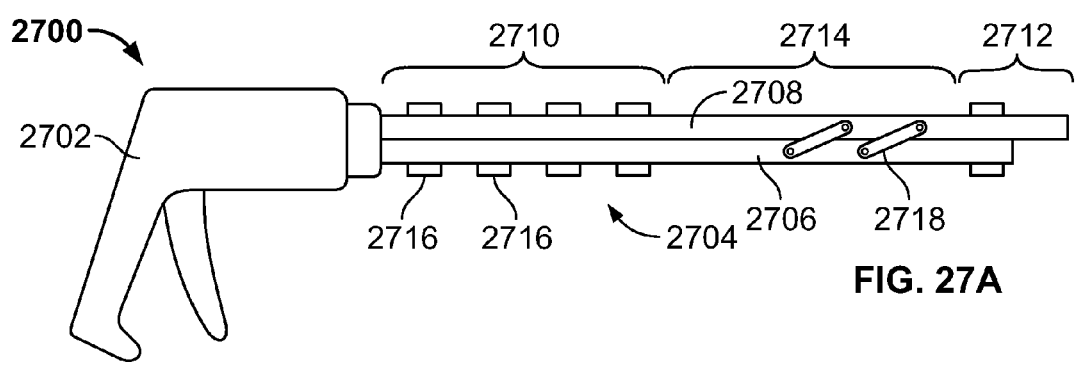
Figure 27B:
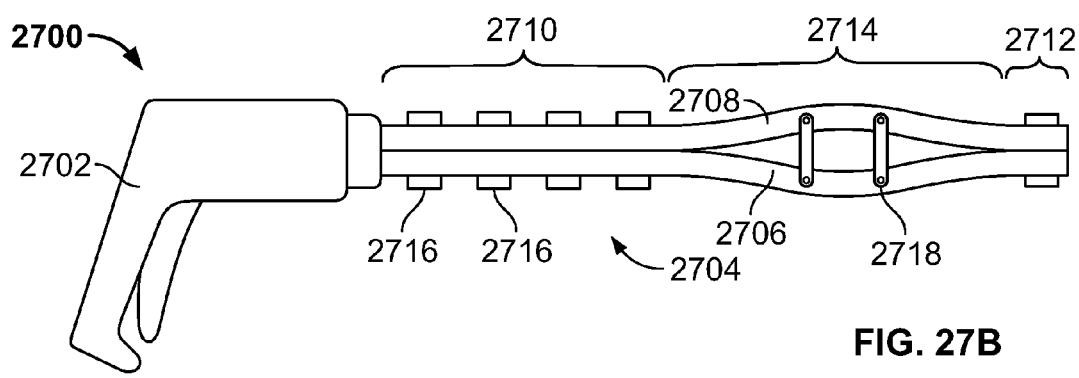

While shown in FIGS. 26A and 26B as having one constrained region and one expandable region, the plate assemblies described here may have any suitable number of constrained regions (e.g., zero, one, two, or three or more) and expandable regions (e.g., one, two, or three or more), so long as there is at least one expandable region. The number of constrained and expandable regions, as well as their placement, may alter the shape of the plate assembly when in its expanded configuration. For example, FIGS. 27A and 27B show one such variation of dilatation device (2700) comprising handle portion (2702) with plate assembly (2704) attached thereto. Plate assembly may comprise first (2706) and second (2708) plate members, and may be divided into proximal (2710) and distal (2712) constrained regions with expandable region (2714) positioned therebetween. The plate members in constrained regions (2710) and (2712) are shown in FIGS. 27A and 27B as connected via rivets (2716), but it should be appreciated that the plate members may be constrained in any suitable manner, as will be described in more detail below. In expandable region (2714), arms (2718) connect the plate members in hinged manner to allow expansion of the expandable region (2714) when device (2700) is actuated. When plate assembly (2704) is changed from a low-profile configuration (as shown in FIG. 27A) to an expanded configuration (as shown in FIG. 27B), the spacing between first (2706) and second (2708) plate members may decrease near the constrained regions (2710) and (2712).

To dilate tissue using device (2700), at least a portion of plate assembly (2704) is advanced to a target location. Distal constrained region (2712) may aid in placement of the device (2700). For example, the device (2700) may be advanced into tissue until the distal constrained region (2712) contacts a tissue surface. If the length of distal constrained region (2712) is known, then a user may be able to determine the location of the expandable region (2714) relative to the tissue surface. Additionally, distal constrained region (2712) may contain one or more structures or features that may temporarily engage tissue to maintain device (2700) at a target location. Once in place, plate assembly may be moved between a low-profile and an expanded configuration, as described in more detail above. As the expandable region (2714) expands, the plate members may push against surrounding tissue to dilate the tissue. The device (2700) may then be returned to a low-profile configuration, and removed from the body.

Figure 28A:
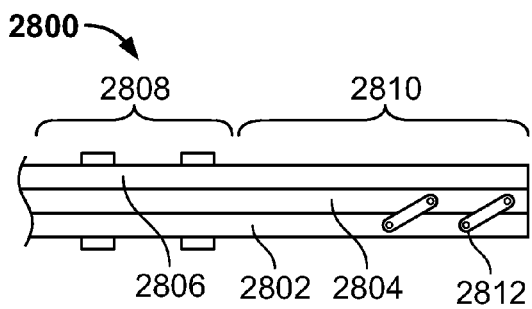
Figure 28B:
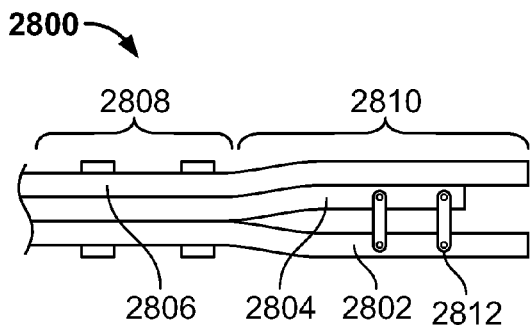

While shown in FIGS. 26A, 26B, 27A and 27B as having two plate members, the plate assemblies described here may comprise any suitable number of plate members. For example, FIGS. 28A-28D illustrate two variations of plate assemblies that comprise three plate members. Specifically, FIGS. 28A and 28B show side views of a distal portion of one variation of plate assembly (2800). In this variation, plate assembly (2800) comprises first plate member (2802), second plate member (2804), and third plate member (2806), and may be divided into a constrained region (2808) and an expandable region (2810). In this variation, arms (2812) may connect first (2802) and second (2804) plate members in a hinged manner in expandable region (2810). Additionally, first (2802) and third (2806) plate members may be fixedly attached relative to a handle portion (not shown), while second plate member (2804) may be movable relative to first (2802) and third (2806) plate members to actuate the plate assembly (2800) between a low-profile configuration (as shown in FIG. 28A) and an expanded configuration (as shown in FIG. 28B). Because the positions of first (2802) and third (2806) plate members are fixed relative to the handle portion, these plate members may press against tissue during expansion without sliding relative to tissue. The expansion of the expandable region (2810) may be used to dilate surrounding tissue, as described in more detail above.

Figure 28C:
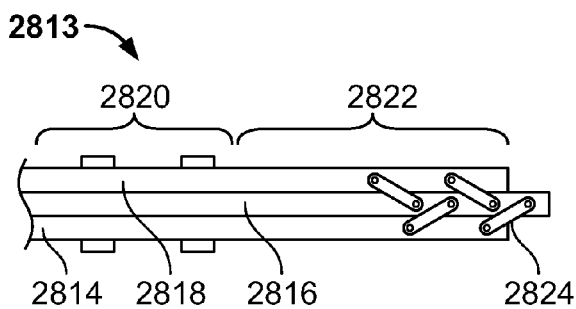
Figure 28D:
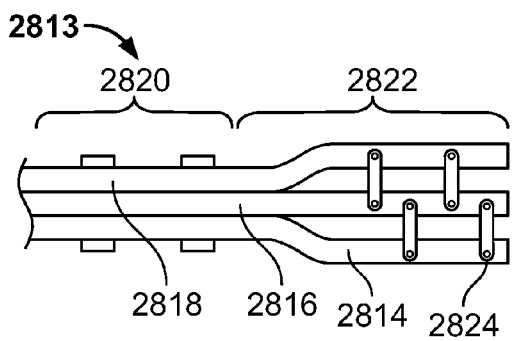

FIGS. 28C and 28D illustrate another variation of plate assembly (2813). In this variation, plate assembly (2813) may comprise first plate member (2814), second plate member (2816), and third plate member (2818), and may be divided into constrained region (2820) and expandable region (2822). In this variation, arms (2824) may connect second plate member (2816) to both first (2814) and third (2818) plate members in a hinged manner within expandable region (2822). As described immediately, first (2814) and third (2818) plate members may be fixedly attached to a handle portion (not shown), while second plate member (2816) may be slidable change the plate assembly between low-profile and expanded configurations (shown in FIGS. 28A and 28B, respectively). Expansion of the expandable region (2822) may occur as a result of the rotation of the arms (2824), as described in more detail above.

Figure 29A:
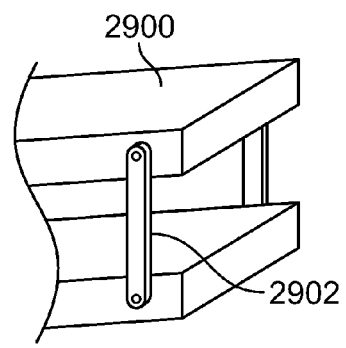
FIGS. 29A-29D show illustrative variations of arm members suitable for use with the plate assemblies described herein.
Figure 29B:
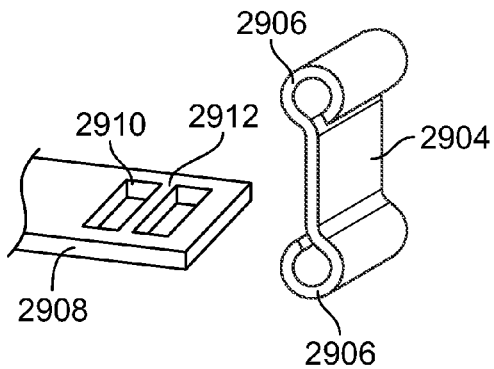
Figure 29C:
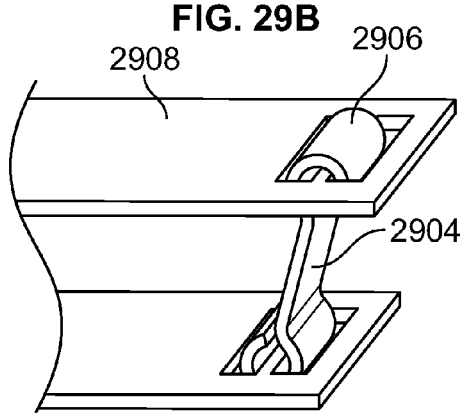
Figure 29D:
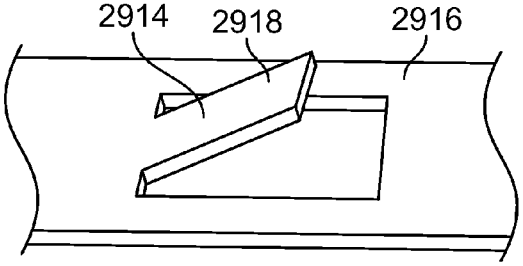
Figure 30A:
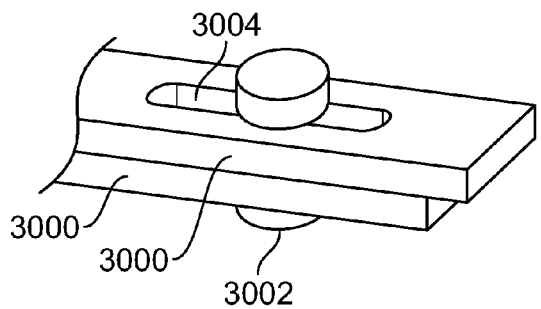
FIGS. 30A-30C, 31A-31C, 32A and 32B illustrate several variations of the devices described here.
Figure 30B:
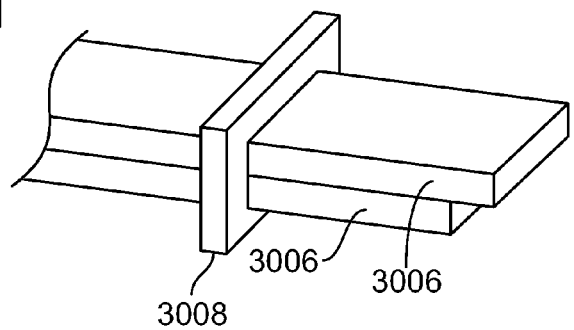
Figure 30C:
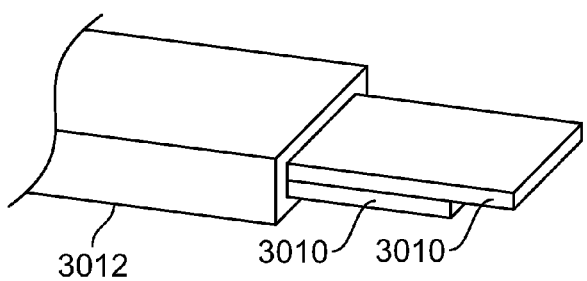

Any number of arms (e.g., one, two, three, four, or five or more) may be used connect plate members in a hinged manner. Each arm may have any suitable size, shape, and configuration. For example, FIG. 29A shows one variation in which plate members (2900) are connected by arms (2902) that are rotatably connected to the sides of the plate members. While shown in FIG. 29A as being straight, arms (2902) need not be. Indeed, in some variations the arms (2902) may be curved, bent, or may follow one or more alternate paths (e.g., a zig-zag path or a sinusoidal path). FIGS. 29B and 29C show another variation in which arm (2904) comprises hook portions (2906) on either end of the arm (2904). In these variations, each plate member (2908) may comprise at least two apertures (2910) that may define a crossbar (2912). The hook portions (2906) of arm (2904) may be placed around the crossbars (2912) of different plate members (2908), as shown in FIG. 29C, allowing hook portions (2906) to rotate relative to the plate members (2908). FIG. 29D shows yet another variation in which arm (2914) is formed from a portion of one or more plate members (2916). In these variations, a strip (2918) may be partially separated from the plate member (2916) such that it can rotate or bend away from the rest of the plate member (2916). The free end of the strip (2918) may then be attached to another strip (not shown) or plate member (not shown), thereby connecting the plate members in a hinged fashion.

Where plate members are held in a constrained fashion, they may be connected in any suitable manner, for example, by one or more constraining elements. FIGS. 30A-30C illustrate different variations of constraining elements suitable for use in the plate assemblies described here. FIG. 30A shows two plate members (3000) joined by a rivet (3002). In these variations, rivet (3002) may at least partially pass through each of the plate members (3000), and may hold the plate members (3000) in approximation to each other. One or more of the plate members (3002) may comprise a track-like aperture (3004) that may allow the plate member (3002) to slide relative to the rivet (3002) and the other plate members.

FIG. 30B shows another variation in which two plate members (3006) are joined via a connector (3008) that at least partially surrounds the plate members (3006). By at least partially surrounding the plate members (3006), the connector (3008) may hold the plate members (3006) in approximation, yet may still allow one or more of the plate members (3006) to slide relative to connector (3008). Additionally, in some variations the connector (3008) may be fixedly connected to one or more plate members (e.g., by welding, soldering, adhesive bonding, or the like), such that the connector is fixedly connected to some plate members and slidably connected to one or more plate members. FIG. 30C shows yet another variation in which plate members (3010) are joined via a sheath (3012). Much as described above in relation to FIG. 30B, sheath (3012) may hold the plate members (3010) in approximation, yet may allow one or more of the plate members (3010) to slide through the sheath (3012).

Figure 31A:
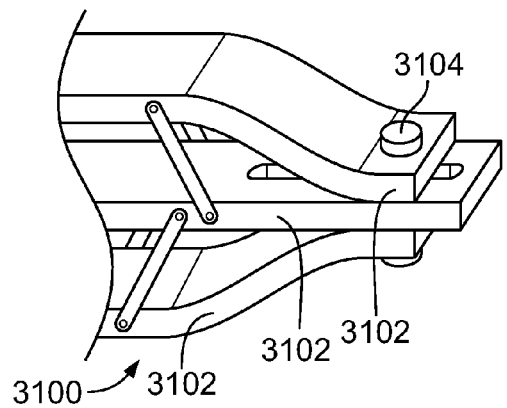
Figure 31B:
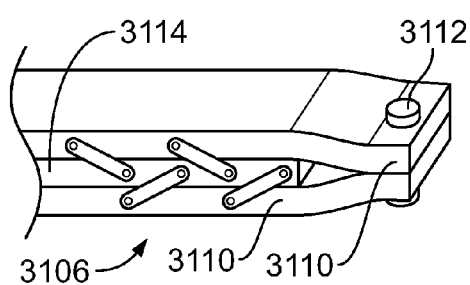
Figure 31C:
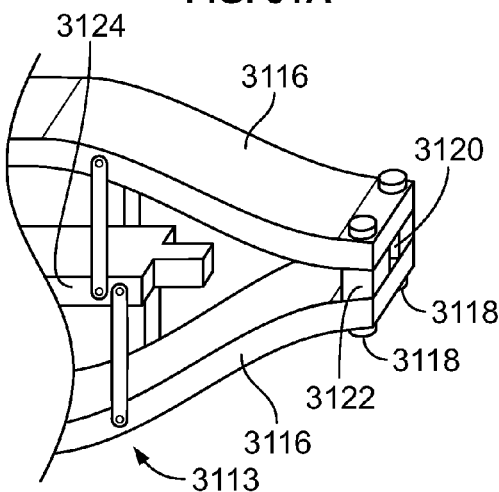

FIGS. 31A-31C illustrate several variations of plate assemblies comprising three plate members that have constrained regions at the distal ends of the plate assemblies. For example, FIG. 31A shows a variation of plate assembly (3100) comprising three plate members (3102), in which all three plate members (3102) are joined via rivet (3104). FIG. 31B illustrates a variation of plate assembly (3106) in which only the outer plate members (3110) are connected via constraining element (3112). In this variation, middle plate member (3114) does not extend to the distal end of the plate assembly (3106). FIG. 31C shows another variation of plate assembly (3113) in which only the outer plate members (3116) are connected via constraining elements (3118). In this variation, the outer plate members (3116) are connected such that they form an aperture (3120) between the two plates. This aperture (3120) may be formed, for example, by placing one or more spacers (3122) between the outer plate members (3116). Alternatively, the aperture (3120) may be formed by one or more channels formed in the outer plate members (3116) In variations having aperture (3120), at least a portion of a third plate member (3124) may be able to pass through aperture (3120) when the device is in its low-profile configuration.

The plate members described herein may have any suitable size or dimensions. Each plate member may or may not be flat, and may have any suitable cross-section shape (e.g., rectangular, squared, triangular, oval, etc.). In some variations, the cross-sectional area may vary along different lengths of the plate member. For example, in some variations a plate member may be wider in an expandable region than in a constrained region. The wider portion of the plate member may provide additionally surface area for contacting tissue. Conversely, the narrow portion of the plate member may provide extra flexibility to the plate member, which may be helpful in navigating the plate assembly in the body. In some variations, one or more surfaces of one or more plate members may be textured, may be configured to release one or more drugs, or may comprise one or more coatings. For example, in some variations one or more plates may be coated with Teflon or a different lubricious material that may help facilitate sliding between adjacent plate members. Plate members may be made of any suitable materials, such as, for example, stainless steel, cobalt chrome, metal alloys (e.g., nickel-cobalt alloys, nickel-titanium alloys, copper-aluminum-nickel alloys, copper-zinc-aluminum-nickel alloys, etc.), nylon-reinforced polymer extrusions, Kevlar-reinforced polymer extrusions, combinations thereof and the like. The plate assemblies may also comprise a cover, such as those described in more detail above.

Figure 32A:
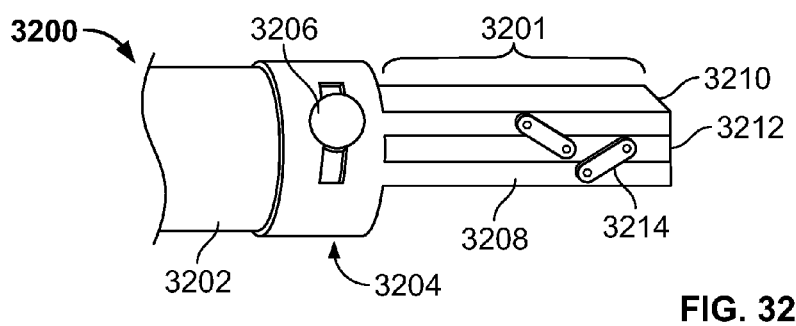
Figure 32B:
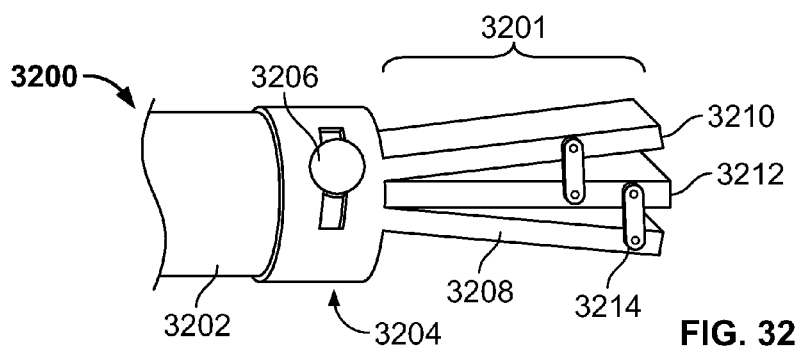

Because the plate assemblies described above only expand within a single plane, it may be desirable to make the plate assembly rotatable such that it may be rotated to dilate tissues in other planes. As such, any of the plate assemblies described above may be configured to rotate relative to one or more portions of the dilatation device, but need not be. FIGS. 32A and 32B illustrate another variation of dilation device (3200) with a rotatable dilating portion (3201). Shown there is cannula (3202) with a cap assembly (3204) rotatably attached. Although shown in FIGS. 32A and 32B as being rotatably attached via rivets (3206), the cannula (3202) and cap assembly (3204) may be attached in any suitable manner. Cap assembly (3204) may have first (3208) and second (3210) plate members attached thereto. First (3208) and second (3210) plate members may be attached to a third plate member (3212) in a hinged manner via arms (3214). At least a portion of the third plate member (3212) may extend through cannula (3202) to a handle portion (not shown), and may be advanced or withdrawn relative to cap assembly (3204). This movement may cause arms (3214) to rotate, which may change dilating portion (3201) from a low profile configuration (as shown in FIG. 32A) to and expanded configuration (as shown in FIG. 32B).

Additionally, third plate member (3212) may be used to rotate the cap assembly (3204) relative to cannula (3202). Specifically, third plate member (3212) may be rotated within sheath (3202), and the connection with the first (3208) and second (3210) plate members may rotate the cap assembly (3204) relative to sheath (3202). This rotation may allow the device (3200) to dilate tissue in multiple planes. For example, the dilating portion (3201) may be advanced in a low-profile configuration to a target tissue. The third plate member (3212) may be withdrawn to move dilating portion (3201) to an expanded configuration, thereby dilating tissue in a first plane. The dilating portion (3201) may then be returned to a low-profile configuration, and the cap assembly (3204) may be rotated as described above. At this point, the dilating portion (3201) may again be changed to an expanded configuration, dilating tissue in a second plane. This procedure may be repeated as necessary for any number of planes. In some variations, the cap assembly (3204) may rotate automatically upon actuation of the device.

Figure 33A:
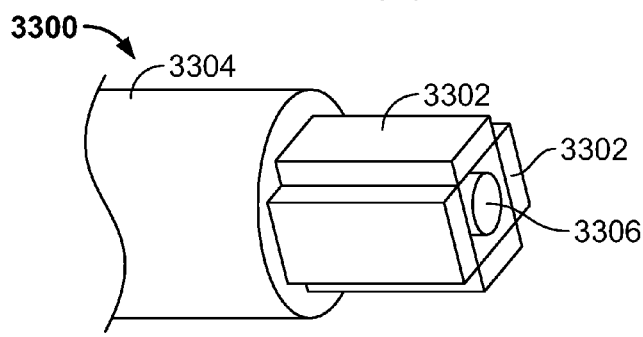
FIGS. 33A and 33B depict a side view and a cross-sectional side view, respectively, of one variation of the devices described here.
Figure 33B:
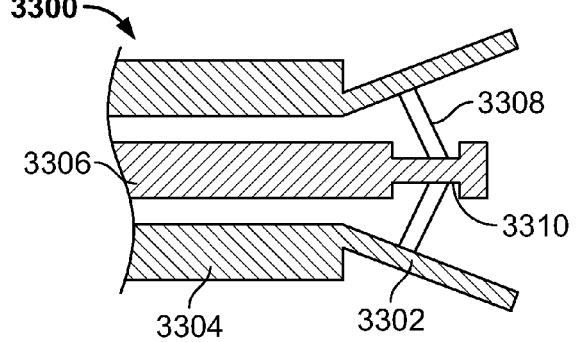
Figure 33C:
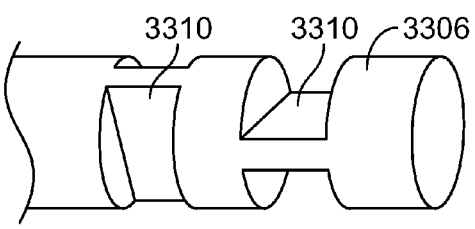
FIG. 33C shows a perspective view of one component of device depicted in FIGS. 33A and 33B.

In other variations, the dilatation devices may be configured to dilate tissue in multiple planes simultaneously. For example, FIGS. 33A-33C illustrate one such variation of the dilation device (3300) in which four plate members (3302) are hingedly attached to the distal end of a cannula (3304). A cylindrical inner member (3306) may be disposed at least partially within cannula (3304), and may be hingedly attached to the plate members (3302) via arms (3308). The inner member (3306) may be withdrawn (or advanced) relative to sheath (3304) to expand plate members (3302) from an unexpanded configuration (as shown in FIG. 33A) to an expanded configuration (as shown in a cross-sectional side view in FIG. 33B) for dilating tissue. FIG. 33C shows a perspective view of the distal end of inner member (3306). As shown there, inner member (3306) comprises one or more flat portions (3310) onto which one or more arms (not shown) may be hingedly attached. These flat portions may have different radial orientations, which may allow the arms to push against plate members (3302) in different directions. This in turn may allow plate members (3302) to dilate tissue in multiple planes simultaneously. Thus, to dilate tissue, the device (3300) may be advanced to a target location in the body, and the inner member (3306) may be withdrawn or advanced to expand the plate members (3302) from a low-profile to an expanded configuration. This expansion may press against tissue, which may in turn dilate surrounding tissue.

Still other variations of the dilatation devices described here may comprise one or more expandable tubes or hoops. FIGS. 9A-9C illustrate one such variation of dilatation device (900). FIG. 9A shows a perspective view of a portion of dilatation device (900), comprising winder (902) and hoop (904). Hoop (904) may comprise casing (908), and may or may not comprise one or more slots (906). Generally, a portion of winder (902) may be configured to be placed and held within casing (908). Additionally, a portion of the hoop (904) may pass through casing (908), and winder (902) may engage the portion of hoop (904) passing through casing (908). In variations where the hoop (904) comprises one or more slots (906), the winder (902) may comprise threading (not shown) that engages the one or more slots. As winder (902) is rotated relative to casing (908), the engagement between winder (902) and hoop (904) may cause a portion of the hoop (904) to pass through casing (908), thereby either reducing or increasing the outer diameter of hoop (904).

To dilate tissue using dilatation device (900), winder (902) may be rotated to reduce the outer diameter of hoop (904) to a low-profile configuration, as shown in a side view in FIG. 9B. The hoop (904) may then be advanced into the body to a target site. In some variations, casing (908) may be attached to the outer surface of a catheter (not shown), and the hoop (904) may surround at least a portion of the catheter. In other variations, casing (908) may be attached to a catheter such that casing (908) and hoop (904) extend beyond the distal end of the catheter. Winder (902) may or may not pass through a lumen in the catheter. Once the dilatation device (900) is in place, winder (902) may be rotated relative to casing (908). This rotation may cause a portion of the hoop (904) to pass out of casing (908), thereby increasing the outer diameter of hoop (904) and changing hoop (904) to an expanded configuration, as shown in a side view in FIG. 9C. As the hoop (904) is expanded, tissue sounding hoop (904) may be dilated.

FIGS. 10A and 10B illustrate another variation of dilatation device (1000) comprising tube (1002) having slit (1004) and rods (1006). When tube (1002) is in an unexpanded configuration, as shown in FIG. 10A, at least a portion of rods (1006) may be disposed within one or more lumens (1008) inside of tube (1002). Tube (1002) may be expanded to an expanded configuration, which may cause at least a portion of rods (1006) to be released from the lumens (1008), as shown in FIG. 10B. While shown in FIGS. 10A and 10B as having rods (1006) and lumens (1008), tube (1002) need not. In variations that do include rods (1006), tube (1002) may comprise any number of rods (1006) (e.g., zero, one, two, or three or more rods), and each rod (1006) may have any suitable size, shape, or configuration. Additionally, rods (1006) may have one or more locking structures that may hold tube (1002) in its expanded configuration. Generally, rods (1006) may help prevent tissue from entering the space (1010) created by slit (1004) as tube (1002) is expanded to its expanded configuration.

In other variations of dilatation devices comprising an expandable tube, the tube may be divided into multiple segments. FIGS. 11A and 11B illustrate one such variation of dilatation device (1100) comprising tube (1102). Shown there is tube (1102) comprising first (1104) and second (1106) tube segments connected via hinged arms (1108). Hinged arms (1108) may be configured to allow relative movement between first (1104) and second (1106) tube segments. When hinged arms (1108) are bent, first (1104) and second (1106) tube segments may be brought into close proximity, as shown in FIG. 11A. On the other hand, when hinged arms (1108) are straightened, first (1104) and second (1106) tube segments may be moved away from each other, thereby changing tube (1102) to an expanded configuration, as shown in FIG. 11B. When this expansion occurs within the body, tube segments may act to separate one or more tissues.

Figure 12A:
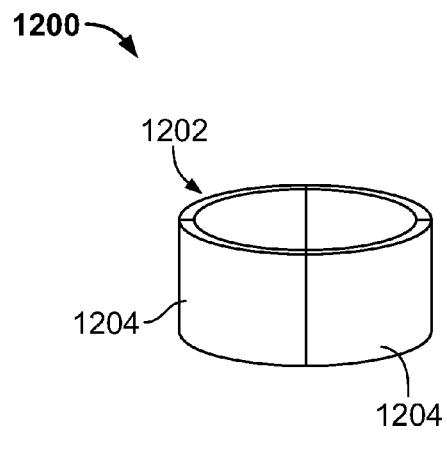
Figure 12B:
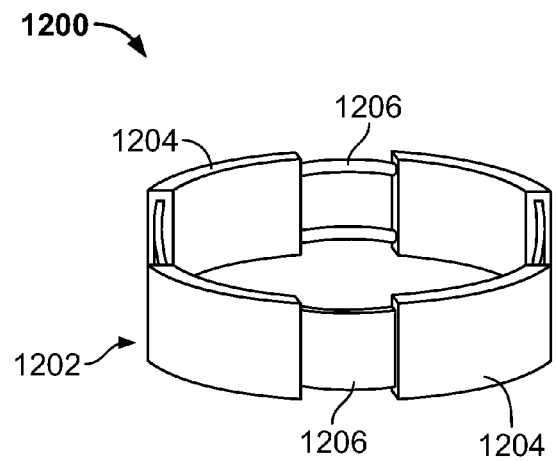

While shown in FIGS. 11A and 11B as having two (first and second) tube segments, the expandable tube (1102) may comprise any number of discrete segments (e.g. one, two, three, four, or five or more). Similarly, although shown in FIGS. 11A and 11B as being connected via hinged arms (1108), the tube segments may be connected in any suitable manner. In some variations, tube sections may be connected via one or more rods, such as those described in relation to FIGS. 10A and 10B as described above. Indeed, FIGS. 12A and 12B illustrate one such variation of dilatation device (1200) comprising tube (1202). FIG. 12A shows tube (1202) in an unexpanded configuration. As shown there, tube (1202) is divided into four tube segments (1204). Each tube segment (1204) may comprise one or more rods (1206), one or lumens (not shown), or a combination thereof. When tube segments (1204) are connected, each rod (1206) of a given tube segment (1204) may fit at least partially within one or more lumens of an adjacent tube segment (1204). When tube (1202) is expanded, tube segments (1204) may move away from each other, but may remain connected via rods (1206), as shown in FIG. 12B.

Figure 13A:
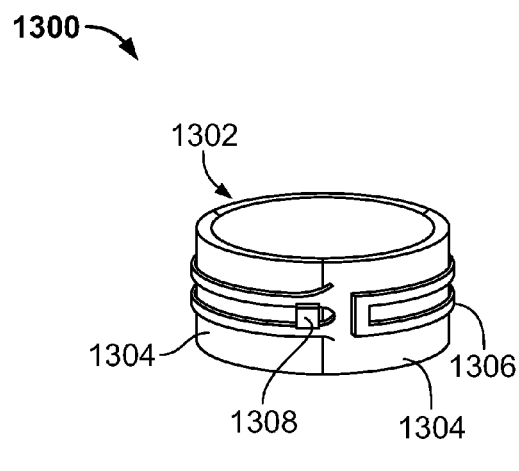
Figure 13B:
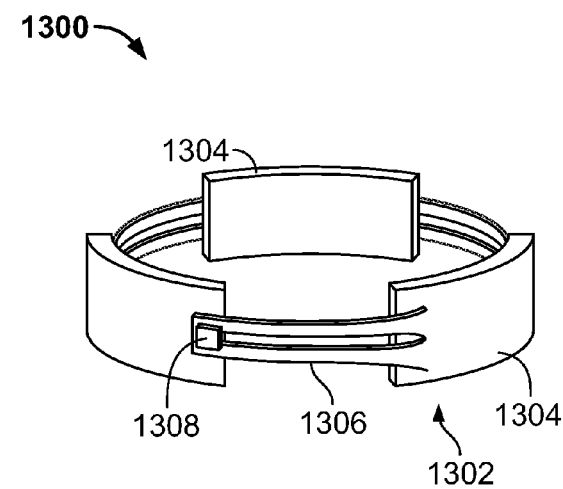

In other variations, the different tube segments may be connected via one or more tracks. FIGS. 13A and 13B show one such variation of dilatation device (1300) comprising tube (1302). FIG. 13A shows tube (1302) in an unexpanded configuration. As shown there, tube (1302) is divided into three tube segments (1304) comprising tracks (1306) and knobs (1308). Each tube segment (1304) may have one or more tracks (1306), one or more knobs (1308), or a combination thereof. When tube segments (1304) are connected, one or more knobs (1308) on one tube segment (1304) may slidably engage one or more tracks (1306) on an adjacent tube segment (1304). When tube (1302) is expanded, tube segments (1304) may move away from each other, but may be connected due to the sliding engagement between knobs (1308) and tracks (1306).

While shown in FIGS. 10A-13B as having expandable tubes that are cylindrical, the dilatation devices may comprise expandable tubes having any suitable cross-sectional shape. Examples of suitable cross-sectional shapes include, but are not limited to, circles, ellipses, triangles, rectangles, polygons, shapes with irregular geometry, combinations thereof, or the like.

Any of the expandable tubes described above may be used to dilate one or more tissues. In some variations, the expandable tube may be disposed around or otherwise attached to a portion of a catheter. FIGS. 20A and 20B show one variation of dilatation device (2000), comprising catheter (2002) and tube (2004). As shown in FIG. 20A, tube (2004) comprises tube segments (2006), tracks (2008) and knobs (2010), and is disposed around the outer surface of catheter (2002). At least a portion of tube (2004) may be releasably or permanently attached to catheter (2002). In some variations, expansion of tube (2004) may cause to tube (2004) to disengage from catheter (2002). In other variations, one or more tube segments (2006) may remain attached to catheter (2002) when tube (2004) is expanded, as shown in FIG. 20B.

In other variations, the expandable tube may be attached to the end of a catheter. FIGS. 21A and 21B show two such variations of dilatation device (2100) comprising catheter (2102), tube (2104), and implant (2106). As shown in FIG. 21A, tube (2104) comprises tube segments (2108) and rods (2109), and is attached to the end of catheter (2102) via wire (2110) that may pass at least partially through tube (2104) and catheter (2102). While shown in FIGS. 21A and 21B as being attached to catheter via wire (2110), tube (2104) may be attached in any suitable manner (e.g. adhesives, mechanical fastening). Expansion of the tube (2104) may cause implant (2106) to expand, as shown in FIG. 21B. This expansion of implant (2106) may help provide apposition between implant (2106) and surrounding tissue. Additionally, in some variations, expansion of tube (2104) may cause to tube (2104) to disengage from catheter (2102). In other variations, one or more tube segments (2108) may remain attached to catheter (2102) when tube (2104) is expanded, as shown in FIG. 21B. In variations in which tube (2104) comprises a wire (2110), the wire (2110) may be withdrawn through tube (2104) to release tube (2104) from dilatation device (2100).

Generally, the expandable tube may be advanced in an unexpanded configuration to a target location in the body. Once in place, the expandable tube may be expanded to an expanded configuration, and may thereby dilate surrounding tissue. The expandable tube may be expanded in any suitable manner. In some variations, a balloon or other expandable device may be expanded within the interior of the expandable tube, which may thereby open the expandable tube. In variations where the expandable tube comprises one or more rods and lumens, as described above, one or more balloons or other expandable structure may be disposed within one or more of the lumens. Inflation or expansion of a balloon or other expandable structure within a lumen may push against a rod disposed in that lumen. This may, in turn, force a portion of the rod to exit the lumen, which may cause the tube to expand.

Once the expandable tube has been expanded to dilate tissue, the expandable tube may or may not be removed from body. In some variations, the expandable tube may be disengaged from the rest of the dilatation device, and may thereby be released in the body. In some of these variations, the expandable tube may have one or more features that hold it in its expanded configuration. For example, in variations where the expandable tube comprises one or more tracks and knobs, the track may be configured such that a knob can only slide through the track in one direction. Additionally, the expandable tube may comprise one or more prongs, barbs, or anchors, as described above, which may help to fix the expandable tube relative to one or more tissues. For example, as the expandable tube is expanded, it may be brought into apposition with tissue. As this apposition occurs, one or more anchors, barbs, or prongs may be pushed into the tissue, thereby causing the expandable tube to engage the surrounding tissue. Furthermore, the tube may or may not be biodegradable, and may or may not be later removed via aspiration or by another suitable manner. When released in the body, the tube may provide one or more functions in the body, such as drug delivery, stenting, or acting as a marker.

Figure 14A:
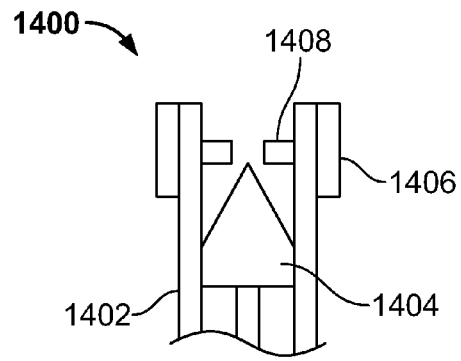
FIGS. 14A and 14C show cross-sectional side views of a suitable variation of the devices described here.
Figure 14C:
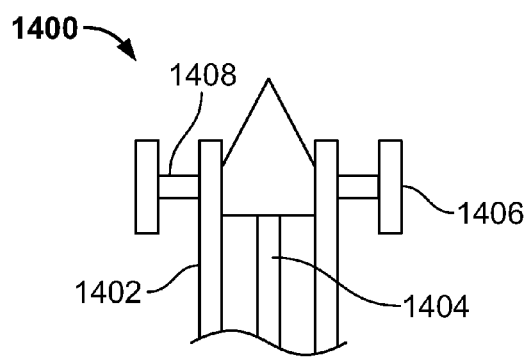
Figure 14B:
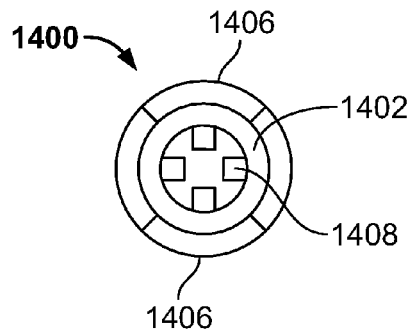
FIGS. 14B and 14D are frontal views of the device of FIGS. 14A and 14C.
Figure 14D:
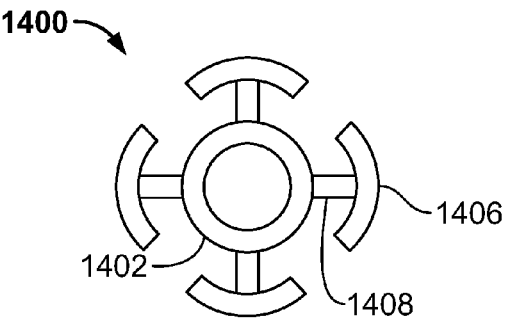

Some variations of the dilatation devices described here comprise a catheter with expandable sections attached thereto. FIGS. 14A-14D illustrate one variation of dilatation device (1400), comprising catheter (1402), tapered pusher (1404), and plates (1406) having pegs (1408). Pegs (1408) may be slidably disposed within apertures (not shown) in the body of catheter (1402). This engagement between pegs (1408) and catheter (1402) may allow plates (1406) to move relative to catheter (1402). FIGS. 14A and 14B show a cross-sectional side view and a front view, respectively, of dilatation device (1400) in a low-profile configuration, in which plates (1406) are positioned adjacent catheter (1402). Dilatation device (1400) may be advanced in a low profile configuration to a target site, and then plates (1406) may be expanded to dilate tissue at the target site. To expand plates (1406), tapered pusher (1404) may be advanced through catheter (1402). As tapered pusher (1404) is advanced through catheter (1402), the tapered pusher (1404) may engage pegs (1408) and may gradually push pegs (1408) out of catheter (1402), as shown in a cross-sectional side view and a front view in FIGS. 14C and 14D. As pegs (1408) are pushed out of catheter (1402), plates (1406) are also pushed away from catheter (1402) and may thereby dilate tissue.

FIGS. 22A-22D illustrate another variation of dilatation device (2200), comprising catheter (2202), plates (2204), hinged arms (2206), expandable cover (2208), and pushrod (2210) having head (2212). Hinged arms (2206) may be at least partially disposed within tracks (2214) in catheter (2202), and may connect plates (2204) to catheter (2202). Additionally, plates (2204) may be able to rotate relative to hinged arms (2206), which in turn may be able to rotate relative to catheter (2202). This engagement between hinged arms (2206) and catheter (2202) may allow plates (2204) to move relative to catheter (2202). FIGS. 22A and 22B show a perspective view and a cross-sectional side view, respectively, of dilatation device (2200) in a low-profile configuration in which plates (2204) are positioned adjacent catheter (2202). Dilatation device (2200) may be advanced in a low-profile configuration to a target site, and then plates (2204) may be expanded to dilate tissue at the target site. To expand plates (2204), pushrod (2210) may be pulled through catheter (2202). As pushrod (2210) is pulled through catheter, head (2212) may engage hinged arms (2206), which may cause hinged arms (2206) to rotate away from catheter (2202), as shown in a perspective view and a cross-sectional side view in FIGS. 22C and 22D. As hinged arms (2206) rotate away from catheter (2202), plates (2202) are moved away from catheter (2202), and may thereby dilate tissue.

While shown in FIGS. 22A-22D as having an expandable cover (2208), dilatation device (2200) need not. In variations that do include an expandable cover (2208), the expandable cover may serve one or more functions. In some instances, the expandable cover (2208) may be used to support or dilate tissues that are not in direct contact with one or more plates (2204). As can be seen in FIG. 22C, the expandable cover (2208) may span the distance between adjacent plates (2204), and may dilate tissues in that space. In other instances, the expandable cover (2208) may help return dilatation device (2200) to its low-profile configuration. More specifically, the expandable cover (2208) may be made from one or more materials that have a tendency to return to an unexpanded state. In these variations, the expandable cover (2208) may pull plates (2204) back toward catheter (2202). When pushrod (2210) is no longer in contact with hinged arms (2206) (e.g., when pushrod (2210) is moved back to its original position as shown in FIG. 22B, or when pushrod (2210) is pulled past hinged arms (2206)), the expandable cover (2208) may pull plates back into apposition with catheter (2202). It should be noted that any of the dilatation devices described here may comprise one or more expandable covers.

Figure 16A:
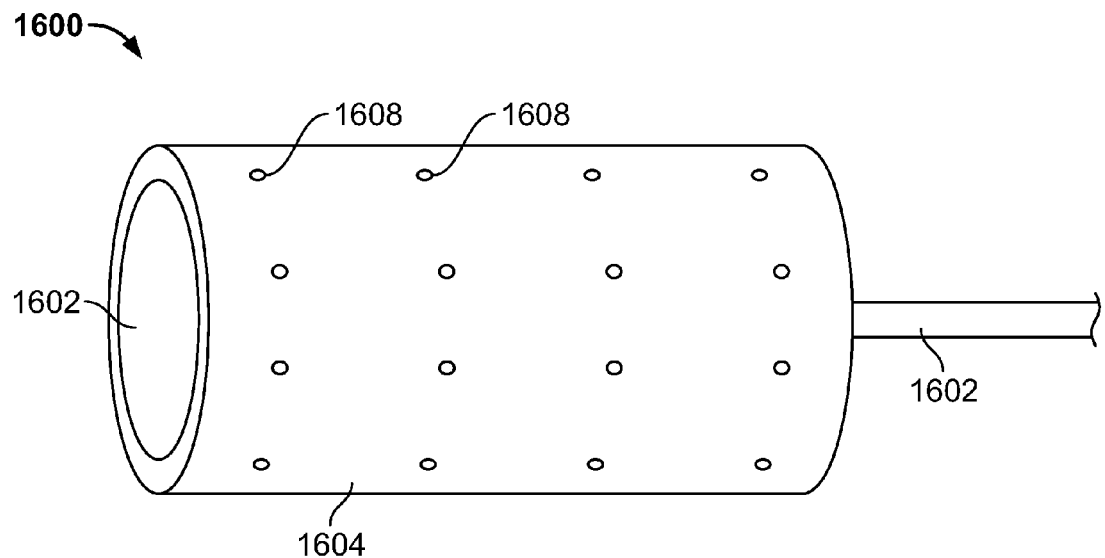
FIGS. 16A and 16B show a side view and a cross-sectional side view, respectively, of a gel- or fluid-releasing tube that may be useful with the dilatation devices described here.
Figure 16B:
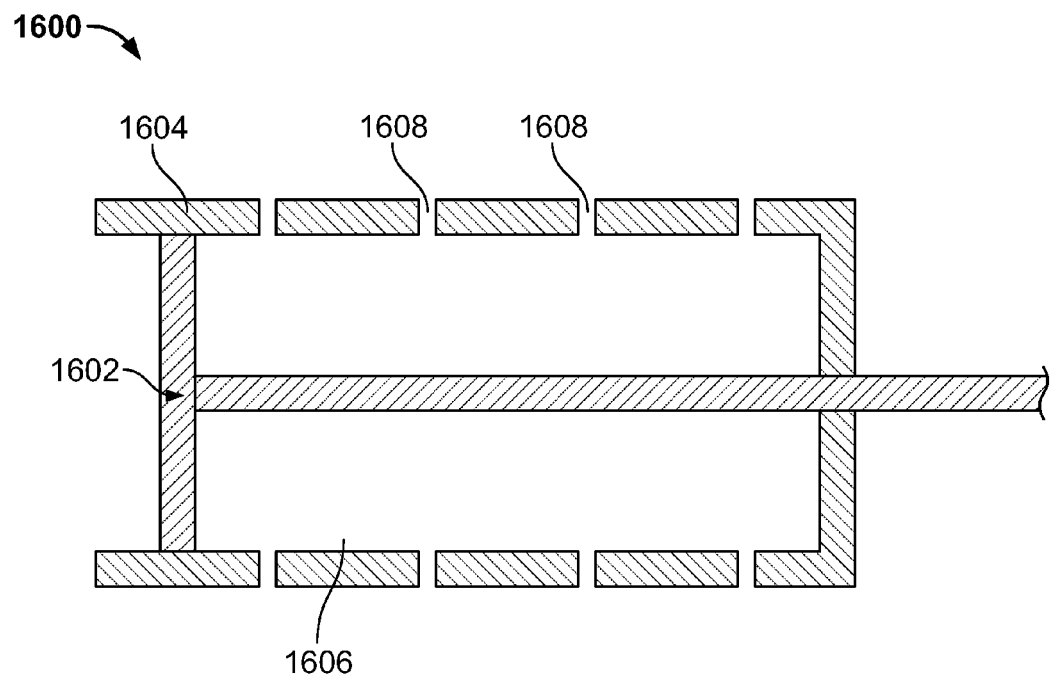

Some variations of the dilatation device described here may release one or more substances that may help facilitate holding dilated tissue in a dilated configuration. In some of these variations, the dilatation device may release one or more fluids or gels that may solidify when released from the dilation device. FIGS. 16A and 16B illustrate a side view and a cross-sectional side view, respectively, of a portion of one such variation of dilatation device (1600). Shown there are plunger (1602) and tube (1604) comprising inner chamber (1606) and apertures (1608). One or more fluids or gels may be held within inner chamber (1606). In some variations, the fluid or gel may be sufficiently viscous such that the fluid or gel does not substantially exit through apertures (1608) when no pressure is applied to plunger (1602). In other variations, a sheath (not shown) may surround tube (1604) to prevent a fluid or gel from prematurely exiting tube (1604) via apertures (1608). In still other variations, a membrane or film may be disposed over one or more apertures. This membrane or film may form a seal over apertures (1608) that may prevent the fluid or gel from passing through the apertures (1608). In some of these variations, the seal may be broken when a certain pressure or force is applied thereto.

Generally, one or more tissues may be dilated using any of the devices or methods as described above. Once dilated, the fluid- or gel-releasing tube (1604) may be moved into the dilated tissue. In variations where a sheath covers at least part of tube (1604), the sheath may be withdrawn relative to tube (1604). Plunger (1602) may then be withdrawn through tube (1604), which may in turn reduce the volume of inner chamber (1606). As the volume of inner chamber (1606) is reduced, plunger (1602) may apply pressure to the fluid or gel, which may cause the fluid or gel to exit tube (1604) via apertures (1608). In variations where the apertures are covered by a membrane or film, the pressure applied to the fluid or gel may be sufficient to break the seal created by the membrane or film. As the fluid or gel is released from tube (1604), it may conform to the surrounding anatomy. The fluid or gel may then subsequently solidify, and tube (1604) may be removed from the body. This may, in turn, leave the solidified fluid or gel to hold the tissue in a dilated configuration.

Any suitable material or combination of materials may be released from the fluid- or gel-releasing tube (1604). In some variations, the material or combination of materials may solidify in response to exposure to one or more fluids or chemicals. For example, in some variations water or other moisture present in an anatomical passageway may cause the materials to solidify. In other variations, the material or combination of materials may solidify in response to one or more stimuli. Examples of suitable stimuli include, but are not limited to, heat, irradiation, light, changes in pH, or combinations thereof. In some variations, the materials comprise one or more polymers with crosslinkable endgroups or branches. In some of these variations, the polymers comprise one or more methacrylate ester end groups. In other variations, the polymers comprise branches with methacrylamide or an amino functional group. Examples of suitable materials include, but are not limited to, poly(d,l-lactide)-poly(ethylene glycol)-poly(d,l-lactide) triblock polymers (DLPLA-PEG-DLPLA), mixtures of eight-arm poly(ethylene glycol)-poly(l-lactide) (PEG-PLLA) and poly(ethylene glycol)-poly(d-lactide) (PEG-PDLA) star block copolymers, mixtures of poly(d,l-lactide) (DLPLA) and N-Methyl-2-pyrrolidone (NMP), mixtures comprising some combination of methacrylate-functionalized PEG-PLLA or PEG-PDLA star block copolymers (PEG-PLLA-MA or PEG-PDLA-MA), which have methacrylate groups at the PLA chain ends, and PEG-MA/PLLA or PEG-MA/PDLA start block copolymers, which have methacrylate groups at the PEG chain ends, and the like.

Tube (1604) may have any number of apertures, and these apertures may be placed anywhere along the surface of tube (1604). The placement of apertures may or may not follow a certain pattern or patterns. For example, it may be desirable to have a more apertures (or apertures of a larger size) toward one end of the tube (1604). This may allow for an even distribution of fluid or liquid released along the length of tube (1604) as the plunger (1602) is pulled therethrough.

We claim:

1. A device for dilating a target tissue comprising:
a handle portion;
a plate assembly attached to the handle portion, the plate assembly comprising a first plate member and a second plate member, each of said first and second plate members comprising a deformable, one-piece plate extending between a proximal end and a distal end, wherein the plate assembly comprises an expandable region, and wherein the proximal end of the first plate member is fixed relative to the handle portion and the proximal end of the second plate member is moveable relative to the handle portion; and
at least two arm members formed as separate members from the plate members and hingedly connecting the first plate member to the second plate member in the expandable region;
wherein the expandable region is configured to expand from a low-profile configuration to an expanded configuration by rotation of the at least two arm members and deformation of the first and second plate members when the second plate member is slid relative to the first plate member, and wherein the deformation of said first and second plate members occurs in opposite directions and increases a space therebetween.

2. The device of claim 1 wherein the plate assembly further comprises a first constrained region, wherein the plate assembly comprises one or more constraining elements connecting the first plate member to the second plate member in the first constrained region, and wherein the first constrained region remains in a low-profile configuration when the second plate member is slid relative to the first plate member.

3. The device of claim 2 wherein the one or more constraining elements comprises one or more rivets.

4. The device of claim 2 wherein the one or more constraining elements comprises one or more connectors that at least partially encircle the plate assembly.

5. The device of claim 2, wherein the one or more constraining elements comprises a sheath.

6. The device of claim 2 wherein the plate assembly further comprises a second constrained region that remains in a low-profile configuration when the second plate member is slid relative to the first plate member, and wherein the expandable region is positioned between the first constrained region and the second constrained region.

7. The device of claim 1 wherein the plate assembly further comprises a third plate member.

8. The device of claim 1 further comprising a cover.

9. The device of claim 1 wherein the at least two arm member are one-piece members comprising a first end and a second end, wherein the first end is directly connected to the first plate member and the second end is directly connected to the second plate member to hingedly connect said first plate member to said second plate member in the expandable region.

10. The device of claim 1 wherein the distal end of the first plate member and the distal end of the second plate member are different distances from the handle portion when the expandable region is in the low-profile configuration.

\* \* \* \* \*